US010376274B2

(12) United States Patent
Farin et al.

(10) Patent No.: US 10,376,274 B2
(45) Date of Patent: Aug. 13, 2019

(54) APPARATUS AND METHOD FOR VESSEL OCCLUSION REMOVAL

(71) Applicant: Perflow Medical Ltd., Tel-Aviv (IL)

(72) Inventors: Danny Farin, Adanim (IL); Gilad Cibulski, Zur-Moshe (IL); Avraham Rapaport, Tel-Aviv (IL); Itamar Bonneau, Tel-Aviv (IL)

(73) Assignee: Perflow Medical Ltd., Natania (IL)

( * ) Notice: Subject to any disclaimer, the term of this patent is extended or adjusted under 35 U.S.C. 154(b) by 0 days.

(21) Appl. No.: 15/568,826

(22) PCT Filed: Jul. 14, 2016

(86) PCT No.: PCT/IL2016/050763
§ 371 (c)(1),
(2) Date: Oct. 24, 2017

(87) PCT Pub. No.: WO2017/009841
PCT Pub. Date: Jan. 19, 2017

(65) Prior Publication Data
US 2018/0103970 A1   Apr. 19, 2018

Related U.S. Application Data

(60) Provisional application No. 62/193,204, filed on Jul. 16, 2015.

(51) Int. Cl.
*A61B 17/221* (2006.01)
*A61B 17/12* (2006.01)
(Continued)

(52) U.S. Cl.
CPC ...... *A61B 17/221* (2013.01); *A61B 17/12109* (2013.01); *A61B 17/320725* (2013.01);
(Continued)

(58) Field of Classification Search
CPC .......... A61B 17/320725; A61B 17/221; A61B 2017/22034; A61B 2017/22035;
(Continued)

(56) References Cited

U.S. PATENT DOCUMENTS 4,468,216 A   8/1984   Muto
4,611,594 A   9/1986   Grayhack et al.
(Continued)

FOREIGN PATENT DOCUMENTS

EP   0914807   5/1999
EP   1437097   7/2004
(Continued)

OTHER PUBLICATIONS

International Preliminary Report on Patentability dated Jan. 25, 2018 From the International Bureau of WIPO Re. Application No. PCT/IL2016/050763. (7 Pages).
(Continued)

*Primary Examiner* — Diane D Yabut
*Assistant Examiner* — Majid Jamialahmadi

(57) ABSTRACT

According to an aspect of some embodiments of the present invention there is provided a device for removal of obstructive material from a vessel comprising:
  an expandable structure sized for insertion into the vessel; and
  one or more portion protruding radially from a central longitudinal axis of the expandable structure such that a space between the protrusion and a closest portion of the expandable structure to the portion includes a radial component;
  wherein the space is sized and shaped to be suitable to accept obstructive material.

31 Claims, 22 Drawing Sheets

(51) Int. Cl.
*A61B 17/3207* (2006.01)
*A61B 17/32* (2006.01)
*A61B 17/22* (2006.01)

(52) U.S. Cl.
CPC .......... *A61B 2017/2212* (2013.01); *A61B 2017/22034* (2013.01); *A61B 2017/320064* (2013.01)

(58) Field of Classification Search
CPC .......... A61B 17/12109; A61B 17/3207; A61B 2017/2212; A61B 2017/320064; A61B 2017/2215; A61B 2017/2217; A61M 25/104; A61M 2025/1043
USPC .................................. 606/200, 127, 159
See application file for complete search history.

(56) References Cited

U.S. PATENT DOCUMENTS

| | | | |
|---|---|---|---|
| 4,650,466 A | 3/1987 | Luther | |
| 4,666,426 A | 5/1987 | Aigner | |
| 4,804,358 A | 2/1989 | Karcher et al. | |
| 4,850,969 A | 7/1989 | Jackson | |
| 4,921,483 A | 5/1990 | Wijay et al. | |
| 5,066,282 A | 11/1991 | Wijay et al. | |
| 5,090,960 A | 2/1992 | Don Michael | |
| 5,106,363 A | 4/1992 | Nobuyoshi | |
| 5,149,321 A | 9/1992 | Klatz et al. | |
| 5,158,540 A | 10/1992 | Wijay et al. | |
| 5,184,627 A | 2/1993 | De Toledo | |
| 5,186,713 A | 2/1993 | Raible | |
| 5,217,484 A | 6/1993 | Marks | |
| 5,403,274 A | 4/1995 | Cannon | |
| 5,407,424 A | 4/1995 | LaFontaine et al. | |
| 5,425,723 A | 6/1995 | Wang | |
| 5,451,207 A | 9/1995 | Yock | |
| 5,462,523 A | 10/1995 | Samson et al. | |
| 5,531,715 A | 7/1996 | Engelson et al. | |
| 5,584,804 A | 12/1996 | Klatz et al. | |
| 5,643,228 A | 7/1997 | Schucart et al. | |
| 5,653,684 A | 8/1997 | Laptewicz et al. | |
| 5,888,291 A | 3/1999 | Chopin et al. | |
| 5,954,745 A | 9/1999 | Gertler et al. | |
| 5,972,019 A | 10/1999 | Engelson et al. | |
| 6,044,845 A | 4/2000 | Lewis | |
| 6,066,158 A * | 5/2000 | Engelson ............ A61B 17/221 606/159 | |
| 6,139,517 A | 10/2000 | Macoviak et al. | |
| 6,149,665 A | 11/2000 | Gabbay | |
| 6,258,118 B1 | 7/2001 | Baum et al. | |
| 6,295,990 B1 | 10/2001 | Lewis et al. | |
| 6,481,439 B1 | 11/2002 | Lewis et al. | |
| 6,485,500 B1 | 11/2002 | Kokish et al. | |
| 6,485,522 B1 | 11/2002 | Kokish et al. | |
| 6,595,963 B1 | 7/2003 | Barbut | |
| 6,692,509 B2 | 2/2004 | Wenzel et al. | |
| 7,093,527 B2 | 8/2006 | Rapaport et al. | |
| 7,318,815 B2 | 1/2008 | Qureshi et al. | |
| 7,691,121 B2 | 4/2010 | Rosenbluth et al. | |
| 7,955,344 B2 | 6/2011 | Finitsis | |
| 8,066,757 B2 | 11/2011 | Ferrera et al. | |
| 8,070,791 B2 | 12/2011 | Ferrera et al. | |
| 8,088,140 B2 | 1/2012 | Ferrera et al. | |
| 8,197,493 B2 | 6/2012 | Ferrera et al. | |
| 2001/0016726 A1 | 8/2001 | Dubrul et al. | |
| 2002/0010487 A1 | 1/2002 | Evans et al. | |
| 2002/0016624 A1 | 2/2002 | Patterson et al. | |
| 2002/0161392 A1 | 10/2002 | Dubrul | |
| 2002/0165574 A1 | 11/2002 | Ressemann et al. | |
| 2003/0028238 A1 | 2/2003 | Burkett et al. | |
| 2003/0208262 A1 | 11/2003 | Gaber et al. | |
| 2004/0082962 A1 | 4/2004 | Demarais et al. | |
| 2004/0153119 A1 | 8/2004 | Kusleika et al. | |
| 2004/0219028 A1 * | 11/2004 | Demarais ....... A61B 17/320725 417/53 | |
| 2006/0058836 A1 | 3/2006 | Bose et al. | |
| 2007/0208367 A1 | 9/2007 | Fiorella et al. | |
| 2008/0249458 A1 | 10/2008 | Yamasaki | |
| 2008/0262598 A1 | 10/2008 | Elmaleh | |
| 2009/0030499 A1 | 1/2009 | Bebb et al. | |
| 2009/0105722 A1 | 4/2009 | Fulkerson et al. | |
| 2009/0105737 A1 | 4/2009 | Fulkerson et al. | |
| 2009/0125053 A1 | 4/2009 | Ferrera et al. | |
| 2009/0187240 A1 | 7/2009 | Clerc et al. | |
| 2009/0198269 A1 | 8/2009 | Hannes et al. | |
| 2009/0292307 A1 | 11/2009 | Razack | |
| 2009/0299393 A1 | 12/2009 | Martin et al. | |
| 2010/0087850 A1 | 4/2010 | Razack | |
| 2010/0114017 A1 | 5/2010 | Lenker et al. | |
| 2010/0114135 A1 | 5/2010 | Wilson et al. | |
| 2010/0160951 A1 | 6/2010 | Madison | |
| 2010/0174309 A1 | 7/2010 | Ferrera et al. | |
| 2010/0217187 A1 | 8/2010 | Fulkerson et al. | |
| 2010/0256600 A1 | 10/2010 | Ferrera et al. | |
| 2010/0318097 A1 | 12/2010 | Ferrera et al. | |
| 2010/0318178 A1 | 12/2010 | Rapaport et al. | |
| 2011/0160742 A1 | 6/2011 | Ferrera et al. | |
| 2011/0160757 A1 | 6/2011 | Ferrera et al. | |
| 2011/0160760 A1 | 6/2011 | Ferrera et al. | |
| 2011/0190797 A1 | 8/2011 | Fulkerson et al. | |
| 2011/0213403 A1 | 9/2011 | Aboytes | |
| 2011/0238106 A1 | 9/2011 | Ferrera et al. | |
| 2011/0319917 A1 | 12/2011 | Ferrera et al. | |
| 2012/0016406 A1 | 1/2012 | Ferrera et al. | |
| 2012/0022576 A1 | 1/2012 | Ferrera et al. | |
| 2012/0041460 A1 | 2/2012 | Ferrera et al. | |
| 2012/0041475 A1 | 2/2012 | Ferrera et al. | |
| 2012/0065660 A1 | 3/2012 | Ferrera et al. | |
| 2012/0089216 A1 | 4/2012 | Rapaport et al. | |
| 2012/0116443 A1 | 5/2012 | Ferrera et al. | |
| 2013/0131690 A1 | 3/2013 | Nagi et al. | |
| 2014/0343585 A1 | 11/2014 | Ferrera et al. | |
| 2014/0371779 A1 * | 12/2014 | Vale ................ A61B 17/12109 606/200 |
| 2015/0182361 A1 | 7/2015 | Ferrera et al. | |

FOREIGN PATENT DOCUMENTS

| | | |
|---|---|---|
| EP | 1915434 | 4/2008 |
| WO | WO 2007/089897 | 8/2007 |
| WO | WO 2010/062363 | 6/2010 |
| WO | WO 2010/075565 | 7/2010 |
| WO | WO 2010/146581 | 12/2010 |
| WO | WO 2012/081020 | 6/2012 |
| WO | WO 2013/109756 | 7/2013 |
| WO | WO 2014/139845 | 9/2014 |
| WO | WO 2015/061365 | 4/2015 |
| WO | WO 2017/009841 | 1/2017 |

OTHER PUBLICATIONS

Advisory Action Before the Filing of an Appeal Brief dated Mar. 29, 2013 From the US Patent and Trademark Office Re. U.S. Appl. No. 12/815,428.
Applicant-Initiated Interview Summary dated Nov. 26, 2014 From the US Patent and Trademark Office Re. U.S. Appl. No. 13/378,053.
Communication Pursuant to Article 94(3) EPC dated May 13, 2013 From the European Patent Office Re. Application No. 10737635.2.
Communication Pursuant to Article 94(3) EPC dated Apr. 30, 2015 From the European Patent Office Re. Application No. 10737635.2.
International Preliminary Report on Patentability dated Oct. 2, 2014 From the International Bureau of WIPO Re. Application No. PCT/US2013/021942.
International Preliminary Report on Patentability dated Dec. 29, 2011 From the International Bureau of WIPO Re. Application No. PCT/IL2010/000470.
International Search Report and the Written Opinion dated May 13, 2013 From the International Searching Authority Re. Application No. PCT/US2013/021942.
International Search Report and the Written Opinion dated Nov. 19, 2010 From the International Searching Authority Re. Application No. PCT/IL2010/000470.

(56) References Cited

OTHER PUBLICATIONS

International Search Report and the Written Opinion dated Sep. 22, 2016 From the International Searching Authority Re. Application No. PCT/IL2016/050763.
International Search Report and the Written Opinion dated Mar. 25, 2013 From the International Searching Authority Re. Application No. PCT/US2013/021746.
Official Action dated Mar. 2, 2012 From the US Patent and Trademark Office Re. U.S. Appl. No. 12/815,428.
Official Action dated Sep. 3, 2014 From the US Patent and Trademark Office Re. U.S. Appl. No. 13/378,053.
Official Action dated Jun. 9, 2015 From the US Patent and Trademark Office Re. U.S. Appl. No. 13/378,053.
Official Action dated Oct. 12, 2012 From the US Patent and Trademark Office Re. U.S. Appl. No. 12/815,428.
Official Action dated Jan. 15, 2015 From the US Patent and Trademark Office Re. U.S. Appl. No. 13/378,053.
Official Action dated May 20, 2015 From the US Patent and Trademark Office Re. U.S. Appl. No. 12/815,428.
Official Action dated Jan. 26, 2015 From the US Patent and Trademark Office Re. U.S. Appl. No. 12/815,428.
Official Action dated Mar. 28, 2014 From the US Patent and Trademark Office Re. U.S. Appl. No. 13/378,053.
Official Action dated Jul. 31, 2014 From the US Patent and Trademark Office Re. U.S. Appl. No. 12/815,428.
Restriction Official Action dated Jun. 25, 2013 From the US Patent and Trademark Office Re. U.S. Appl. No. 13/378,053.
Barreto et al. "Thrombus Burden Is Associated With Clinical Outcome After Intra-Arterial Therapy for Acute Ischemic Stroke", Stroke, 39: 3231-3235, Nov. 28, 2008.
Cassels "Thromboembolic Clots Have Same Composition Regardless of Source", Medscape Medical News, p. 1-3, Aug. 2006.
Jahan "A Novel Self Expanding, Fully Retrievable Flow Restoration Device for Treatment of Acute Ischemic Stroke", Stroke, ePosters Archives, # 417, Mar. 21, 2009.
Kelly et al. "Recanalization of an Acute Middle Cerebral Artery Occlusion Using a Self-Expanding Reconstrainable, Intracranial Microstent as a Temporary Endovascular Bypass", Stroke, 39(6): 1770-1773, Jun. 2008.
Marder et al. "Analysis of Thrombi Retrieved From Cerebral Arteries of Patients With Acute Ischemic Stroke", Stroke, 37(8): 2086-2093, Published Online Jun. 22, 2006.
Nogueira et al. "Endovascular Approaches to Acute Stroke, Part 1: Drugs, Devices and Data", American Journal of Neuroradiology, 30: 649-661, Apr. 2009.
Nogueira et al. "Endovascular Approaches to Acute Stroke, Part 2: A Comprehensive Review of Studies and Trials", American Journal of Neuroradiology, AJNR, 30(5): 859-875, Epub Apr. 22, 2009.
Staylor "The Ongoing Evolution in Device-Based Stroke Intervention: An Interview With Adnan Siddiqui", Medtech Insight, 4(12): 52-54, Apr. 2010.
Staylor et al. "Ischemic Stroke: Prying Open the Treatment Window", Medtech Insight, 4(12): 36-51, Apr. 2010.
Communication Pursuant to Article 94(3) EPC dated Jul. 4, 2018 From the European Patent Office Re. Application No. 16742416.7. (3 Pages).
Communication Pursuant to Article 94(3) EPC dated Nov. 26, 2018 From the European Patent Office Re. Application No. 16742416.7. (3 Pages).

\* cited by examiner

APPARATUS AND METHOD FOR VESSEL OCCLUSION REMOVAL

RELATED APPLICATIONS

This application is a National Phase of PCT Patent Application No. PCT/IL2016/050763 having International filing date of Jul. 14, 2016, which claims the benefit of priority under 35 USC § 119(e) of U.S. Provisional Patent Application No. 62/193,204 filed on Jul. 16, 2015. The contents of the above applications are all incorporated by reference as if fully set forth herein in their entirety.

FIELD AND BACKGROUND OF THE INVENTION

The present invention, in some embodiments thereof, relates to devices and methods for removal of obstructions within lumens, and, more particularly, but not exclusively, to an expandable device for removal of clots from blood vessels.

SUMMARY OF THE INVENTION

According to an aspect of some embodiments of the present invention there is provided a device for removal of obstructive material from a vessel comprising:
an expandable structure sized for insertion into the vessel; and
one or more portion protruding radially from a central longitudinal axis of the expandable structure such that a space between the protrusion and a closest portion of the expandable structure to the portion includes a radial component;
wherein the space is sized and shaped to be suitable to accept obstructive material.

According to some embodiments of the invention, the device includes wires, wherein the one or more protruding portion is a portion of a wire.

According to some embodiments of the invention, the space between the protruding portion and the closest portion of the expandable structure includes a component tangential to the central longitudinal axis of the device.

According to some embodiments of the invention, the space between the protruding portion and the closest portion of the expandable structure includes a component parallel to the central longitudinal axis of the device.

According to some embodiments of the invention, the device includes a woven structure, wherein the protruding portion and the closest portion are a warp and weft wire of the woven structure.

According to some embodiments of the invention, the one or more protruding portion is rounded.

According to some embodiments of the invention, the radial component of the space is between 0.01-0.2 mm.

According to some embodiments of the invention, the central longitudinal axis of the expandable structure is a central longitudinal axis of a largest cylindrical space enclosable within the structure.

According to some embodiments of the invention, the largest cylindrical space is a largest length cylindrical space enclosable within the structure.

According to some embodiments of the invention, the largest cylindrical space is a largest diameter cylindrical space enclosable within the structure.

According to some embodiments of the invention, the largest cylindrical space is a largest volume cylindrical space enclosable within the structure.

According to some embodiments of the invention, the expandable structure is configured to have a collapsed state and a range of expanded shapes, wherein the structure is expandable to a maximally expanded state;
wherein a diameter of the largest cylindrical space in the collapsed state is smaller than a volume of the largest cylindrical space in the maximally expanded state.

According to some embodiments of the invention, the diameter of the largest cylindrical space in the collapsed space is 0.3-2 mm.

According to some embodiments of the invention, the diameter of the largest cylindrical space in the maximally expanded state is 1-7 mm.

According to some embodiments of the invention, the radial component of the space is larger when the structure is in each of the range of expanded states than a radial component of the space when the device is in the collapsed state.

According to some embodiments of the invention, the protruding portion and the closest device portion are coupled at least two junctions, where an axial length of the protruding portion between the two junctions is longer than an axial length of the closest device portion between the two junctions.

According to some embodiments of the invention, the protruding portion and the closes device portion are curved spatially arranged to have a phase difference between the portions.

According to some embodiments of the invention, the expandable structure includes a plurality of protruding portions.

According to some embodiments of the invention, protruding portions are disposed at different radial positions around an axial location along the expandable structure.

According to some embodiments of the invention, one or more of the plurality of protruding portions is dispersed at a different axial location along the expandable structure from one or more other protruding portion.

According to some embodiments of the invention, the structure comprises:
a plurality of wires each wire coupled at a different radial position at a distal and a proximal end of the structure;
wherein each the wire transverses a path from the distal end to the proximal end including changes in radial position;
wherein, during the path, one or more wire passes over one or more other wire and under one or more other wire;
wherein the plurality of wires forms a tubular shaped mesh surface between the distal and proximal ends;
wherein at least one portion of one wire includes a protrusion where the wire path departs protrudes radially away from the tubular shaped mesh surface and then extends axially, defining the space between the portion and the tubular shaped mesh surface.

According to some embodiments of the invention, the path including changes in radial position is a helical path.

According to some embodiments of the invention, the device comprises:
at least one wire loop attached to the proximal end of the structure, extending radially away from the central longitudinal axis;
wherein the space is within the wire loop.

According to some embodiments of the invention, the device comprises:
  a plurality of wire loops each loop attached to the proximal end of the structure;
  wherein the space is between two wire loops.

According to some embodiments of the invention, the device comprises:
  a plurality of wires each wire coupled at a different radial position at a distal and a proximal end of the structure; and
  wherein each the wire transverses a path from the distal end to the proximal end including changes in radial position;
  wherein, during the path, one or more wire passes over one or more other wire and under one or more other wire;
  wherein the plurality of wires forms a tubular shaped mesh surface between the distal and proximal ends;
  wherein one or more wire loop protrudes at least radially from the tubular shaped mesh surface.

According to some embodiments of the invention, the device comprises:
  a plurality of wires each wire coupled at a different radial position at a distal and a proximal end of the structure; and
  wherein each the wire transverses a path from the distal end to the proximal end including changes in radial position;
  wherein, during the path, one or more wire passes over one or more other wire and under one or more other wire;
  wherein the plurality of wires forms a tubular shaped mesh surface between the distal and proximal ends;
  wherein at least one wire includes a protruding portion.

According to some embodiments of the invention, the shape is sized and shaped to be suitable to accept at least a portion of the obstructive material.

According to an aspect of some embodiments of the present invention there is provided a method of removal of obstructive material from a vessel comprising:
  positioning a contracted expandable structure in an axial vicinity of the obstructive material;
  coupling the structure to obstructive material, the obstructive material entering into at least one space between a structure protruding portion and a central longitudinal axis of the device;
  removing the obstructive material from the vessel by removing the structure.

According to some embodiments of the invention, the at least one space is a plurality of spaces.

According to some embodiments of the invention, the plurality of spaces includes spaces at different positions along a longitudinal axis of the structure.

According to some embodiments of the invention, the plurality of spaces includes spaces at different radial positions.

According to some embodiments of the invention, the coupling comprises coupling different portions of the obstructive material each portion into a different of the plurality of spaces.

According to some embodiments of the invention, the coupling comprises expanding the structure.

According to some embodiments of the invention, the expanding comprises increasing a size of the space, in at least one dimension.

According to some embodiments of the invention, the expanding comprises decreasing a size of the space, in at least one dimension.

According to some embodiments of the invention, the at least one space is between a structure protruding portion and a second structure portion.

According to some embodiments of the invention, coupling comprises pulling the expandable structure through an axial vicinity of the obstructive material.

According to some embodiments of the invention, the coupling comprises pushing the expandable structure into the obstructive material.

According to some embodiments of the invention, the method comprises contracting the at least one space, in at least one dimension.

According to some embodiments of the invention, the removing comprises moving the device through portions of the vessel with directional and geometrical changes.

According to some embodiments of the invention, the expanding comprises expanding the device until the device exerts outwards force on the vessel walls.

According to some embodiments of the invention, the device exerts outwards force on the vessel walls during the removing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
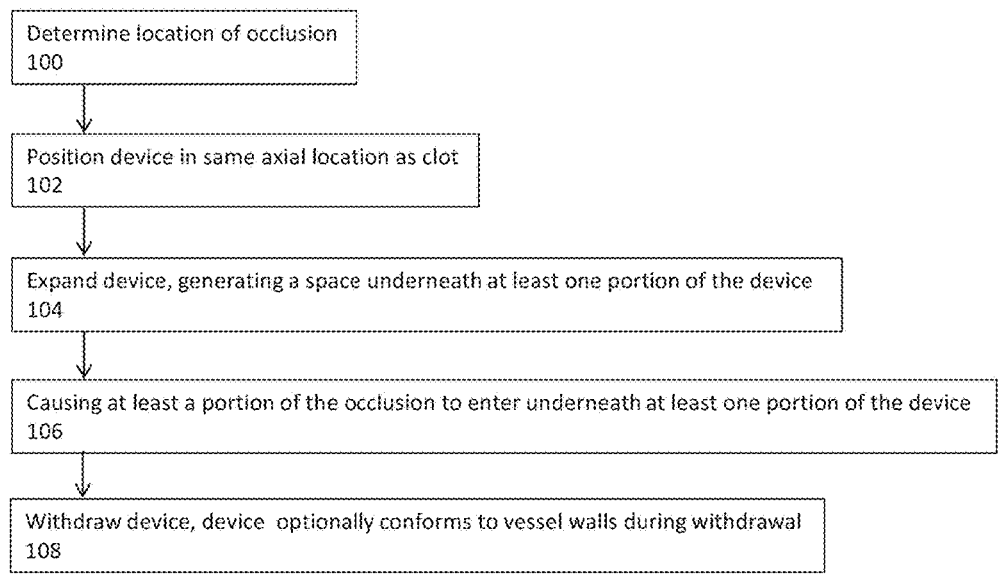
FIG. 1 is a flow chart of an exemplary method of occlusion removal from a vessel, according to some embodiments of the invention.

The present invention, in some embodiments thereof, relates to devices and methods for removal of occlusions within lumens, and, more particularly, but not exclusively, to an expandable device for removal of clots from blood vessels.

Overview

A broad aspect of some embodiments of the invention relates to expandable devices for and methods of removal of obstructions from within blood vessels. In some embodiments, a device is coupled to an obstruction and the device is then removed from the vessel, along with the obstruction.

In some embodiments, coupling between the device and the obstruction is at least partially maintained when the device changes in dimension (e.g. in a radial direction perpendicular to a longitudinal axis of the device) and/or when device bends and/or collapses. For example as, during device removal, the device traverses vascular changes in direction (e.g. bends) and/or geometry.

An aspect of some embodiments of the invention relates to coupling an obstruction to the device by capturing at least a portion of the obstruction (e.g. clot material) underneath a portion of the expandable device. For example, capturing at least a portion of the obstruction within a space in the device which has a radial component (e.g. the space includes a dimension in a radial direction from a central longitudinal axis of the device). For example, capturing at least a portion of the obstruction within a space between a protruding portion (also herein termed "protrusion") and a portion closest to the protruding portion (e.g. with a shortest vector connecting the two portions).

In some embodiments, clot material is captured underneath a radially protruding portion of the device, where the radial direction is measured from a longitudinal central axis of the device. For example, the clot material being captured between (in a radial direction) a longitudinal central axis of the device and the protruding portion.

In some embodiments, a device is expanded within a vessel such that and/or until device protrusion/s contact the vessel walls, for example, capturing obtrusive material underneath the protrusion (e.g. as the device is pulled past the obstructive material). In some embodiments, protrusion/s maintain contact with vessel walls as the device is removed, e.g. during geometrical changes in the vessel (e.g. bends and/or changes in cross sectional area and/or shape).

In embodiments where the device has a non-cylindrical and/or irregular shape (e.g. bent, irregular shaped cross section), the longitudinal central axis is defined as the longitudinal central axis extending from the largest volume (and/or largest diameter and/or largest length) cylinder totally enclosed by the device. Alternatively or additionally, the longitudinal central axis is defined as a line connecting center points of parallel circular cross sections along a length of the device, where at each point along the entirety of the shape's length the circular cross section is the largest circle contained within the device. For example, with a device including a cylindrical mid-portion with a tapered end the longitudinal central axis may be defined as extending through the center of the cylindrical mind-portion and through the central axis of a cone totally enclosed at the tapered end. For example, with a curved and/or bent tubular device, the central longitudinal axis follows the curve of the device.

In some embodiments, obstructive material extends underneath at least one protrusion, where the material enters underneath 30%-95%, or 40%-90%, or 50%-80% or lower or higher or intermediate ranges or percentages, of a length of the protrusion.

In some embodiments, a protrusion is sized to be sufficiently large that clots fit underneath the protrusion. In some embodiments, clots are captured underneath protrusion/s by moving the device within the vessel.

In some embodiments, protrusion/s are rounded, for example, potentially preventing damage to the vessel during expansion of the device and/or movement of the device within the vessel.

An aspect of some embodiments of the invention relates to coupling clot material to the device by capturing a clot in a space between at least two portions of an expandable device, for example between two wires (e.g. nitinol wires). In some embodiments, the space between the portions is sized to be sufficiently large to accept at least a portion of a clot and/or a portion of the clot sufficiently large to couple the clot to the device. In some embodiments, obtrusive material is pinched between the at least two device portions.

In some embodiments, the space includes a radial component.

In some embodiments, an angle between a shortest distance between two wires defining a space and a radial line connecting the protruding wire and the longitudinal central axis is less than 90°, or 5-89°, or 10-85°, or lower, or higher, or intermediate ranges or angles.

In some embodiments, two portions between which clot material is captured include a protruding portion and a nearest (in at least one dimension) second portion of the device to the protruding portion.

In some embodiments, one or more portion defining a space has a different radial separation from a central axis of the device. Additionally, or alternatively, in some embodiments, one or more portion defining a space has a different angular orientation from the device central axis, e.g. a different circumferential location on an outer surface of the device.

In an exemplary embodiment, expanding the device increases a radial space between two device portions whilst a dimension of the space between the portions in a different dimension (e.g. perpendicular to the radial direction) decreases. Movement of the portions, for example, potentially pinching obtrusive material within the space.

In some embodiments, once clot material has entered a space within the device (e.g. between two portions and/or underneath a protrusion), the space is reduced (e.g. in one or more dimension), for example, to hold the clot within the device.

In some embodiments, clot material is captured between more than two portions, for example, 3, or 4, or 5, or 3-10, or smaller or larger or intermediate numbers of portions.

Optionally, in some embodiments, the device is delivered to a clot site within a patient and expanded, for example, to enlarge the space under and/or between portions of the device. Additionally or alternatively, in some embodiments, spaces are enlarged by bending and/or twisting and/or rotating the device.

In an exemplary embodiment, a device includes wire pairs and expansion (and/or bending and/or rotation) of the device causes one of the wires in the wire pair to protrude axially from a central axis of the device more than the other wire in the wire pair.

In some embodiments, once clot material is captured within the device, the device is moved within the vessel, moving clot material held between the device and vessel walls.

In some embodiments, a shape of the device is changed and/or changes as the device is moved within the vessel to maintain contact and/or coupling between the device and the clot material with changing vessel geometry.

In some embodiments, spaces underneath protrusions and/or between portions of the device are sized to be suitable for capture of clot material for a range of device dimensions, potentially enabling clot removal from a range of vessel sizes.

In some embodiments, a size of a space, in one or more dimension, (e.g. suitable for capture of clot material) is 0.005-0.5 mm, or 0.01-0.2 mm, or 0.5-0.1 mm, or lower, or higher or intermediate ranges or sizes.

In some embodiments, the device is expandable to a diameter of (e.g. a device suitable for use within vessels of diameter) 1-7 mm, or 2-6 mm, or 1-5 mm, or lower, or higher or intermediate ranges or sizes. Where the term diameter refers to the diameter of a cylindrical portion of the device and/or an average diameter of and expandable portion of the device and/or diameter of a cylinder entirely enclosed within the expandable device.

In some embodiments, the device includes a collapsed and/or unexpanded diameter of 0.3-2 mm, or 0.3-1.5 mm, or 0.4-1 mm, or lower, or higher or intermediate ranges or sizes.

In some embodiments, a device is expandable to a range of different diameters, where a maximum diameter of the device (e.g. diameter of a largest volume and/or diameter cylinder contained within the device) is 1-7 mm, or 2-6 mm, or 1-5 mm, or lower, or higher or intermediate ranges or sizes.

In some embodiments, a wire pair includes at least two portions (e.g. elongate elements) attached to each other at two points where a length of a first portion and a length of a second portion between the attachment points are different. In some embodiments, changing a shortest distance between the two points (e.g. during device expansion) increases a space between the wires.

In some embodiments, a wire pair includes at least two portions (e.g. elongate elements) each of which includes a curved portion, where the curved portions are spatially arranged with a phase difference, the phase difference generating a space between the portions, at least in one dimension.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Methods of Occlusion Removal

FIG. 1 is a flow chart of an exemplary method of occlusion (e.g. clot) removal from a vessel, according to some embodiments of the invention.

At 100, in some embodiments, a location of a vascular occlusion (also herein termed obstruction) is determined using imaging, for example, using ultrasound (e.g. Duplex ultrasound) and/or MRI and/or CT and/or x-ray imaging.

At 102, a device is positioned in proximity to (also herein termed "in a vicinity of") the occlusion, for example at a position within the vessel such that at least a portion of the device overlaps with the clot in an axial direction of the vessel. For example, where the device positioned 0-30 mm, or 0-10 mm, or 0.5-10 mm, or 1-10 mm, or lower or higher or intermediate ranges or distances from the occlusion.

In some embodiments, a device is introduced into a vessel at a distance from the occlusion and, for example, pushed (e.g. using a sufficiently long elongated element attached to the device) from an introduction site (e.g. an incision) until the device is in proximity to the occlusion, for example at a site of the occlusion. In some embodiments, for example, in the case of a large occlusion extending through a length of the vessel, the device is positioned in a desired position e.g. selected by a physician.

In some embodiments, positioning of the device at the occlusion is guided using imaging (e.g. CT, x-ray, ultrasound, MRI), optionally using contrast material introduced into the vessel.

In an exemplary embodiment, a guide wire is first positioned, a catheter is then inserted over the guide wire and then the device is inserted through the catheter.

In some embodiments, positioning the device in proximity to the occlusion causes at least a portion of the occlusion to be coupled to the device, where, for example, at least a portion of the occlusion enters a space in the device. In some embodiments, at least a portion of the occlusion enters a space radially underneath a portion of the device (e.g. as described herein).

In some embodiments, a portion of the device (e.g. at least a portion of an expandable structure) is pushed through and/or past obstructive material, before being removed. In an exemplary embodiment, at least a portion of an expandable structure in a collapsed configuration is pushed past and/or through obstructive material to be removed. In some embodiments, the structure is then expanded before being removed. In some embodiments, protruding protrusion/s and remove (e.g. "rake") occlusive material as the expandable structure is removed.

At 104, the device is expanded. In some embodiments, expanding the device couples the device with at least a portion of the obstructive material.

In some embodiments, expanding the device generates and/or enlarges at least one space underneath at least one portion of the device. In some embodiments, expanding the device generates a space suitably sized for occlusive material to enter therein.

In some embodiments, one or more space within the device is generated and/or enlarged by twisting and/or bending and/or rotating the device.

In some embodiments, space/s within the device and/or the device (e.g. device diameter and/or maximal radial extent) is expanded by pulling and/or pushing and/or rotating an elongated element attached to the device.

In some embodiments, a space is generated and/or enlarged by a separation of a portion of the device from a central longitudinal axis of the device increasing, for example, size of at least one radial space in the device.

In some embodiments, a space is generated and/or enlarged by a separation between one or more portion of the device increasing at least in one dimension, and, in an exemplary embodiment, at least in a radial dimension.

In some embodiments, expansion of the device increases space/s on a surface of the device (e.g. tangential and/or parallel to the central longitudinal axis) between portion/s of the device.

In some embodiments, expanding the device, for example, includes increasing radial dimensions of the device and/or cross sectional area/s of the device perpendicular to the device long axis (e.g. average cross sectional area of the device). In some embodiments, increasing radial dimension/s of the device corresponds with decreasing a longitudinal length of the device.

At 106, at least a part of the occlusion enters underneath at least one portion of the device.

In some embodiments, expanding the device causes at least a portion of the occlusion to enter the device, for example, to enter a space axially underneath a portion of the device (e.g. a space axially closer to a longitudinal central axis of the device).

In some embodiments, expanding the device causes a separation between two portions of the device to increase (e.g. as described above regarding FIG. 2B), occlusive material entering therein.

Additionally or alternatively, in some embodiments, inserting the device causes material to enter underneath one or more portion of the device.

Alternatively or additionally, in some embodiments, during and/or after expansion and/or insertion of the device, the device is moved (e.g. rotated about the central longitudinal axis and/or moved axially within the vessel) causing occlusive material to enter into space/s within the device.

Optionally, in some embodiments, the device is then contracted (e.g. partially contracted), reducing space/s into which clot material has entered in size (e.g. at least in one dimension), for example, trapping and/or holding the clot material under and/or between portions of the device. In some embodiments, the device is contracted before the device is removed and/or during removal of the device.

At 106, in some embodiments, the device is withdrawn (e.g. by pulling an elongated element attached to the device). In some embodiments withdrawal of the device reduces size of the space/s potentially holding occlusive material therein. Optionally, in some embodiments, the device conforms to vessel wall shape e.g. changing cross sectional area and/or conforming to bends in the vessel, potentially holding a clot between the device and the vessel wall.

Exemplary Device Space/s

Figure 2A:
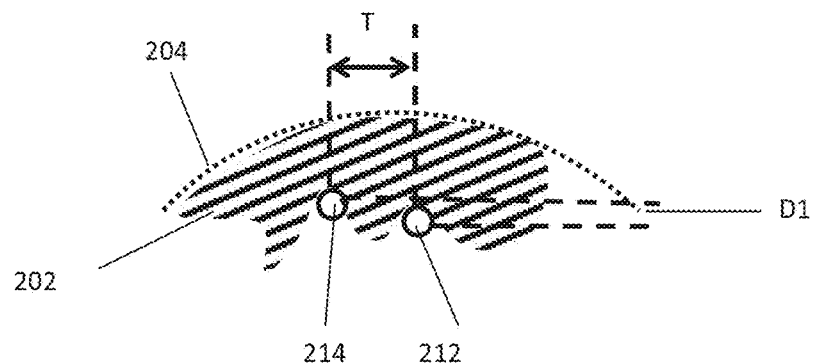
FIG. 2A is a simplified schematic cross sectional view of two portions of a device, within a vessel with an occlusion, according to some embodiments of the invention.
Figure 2B:
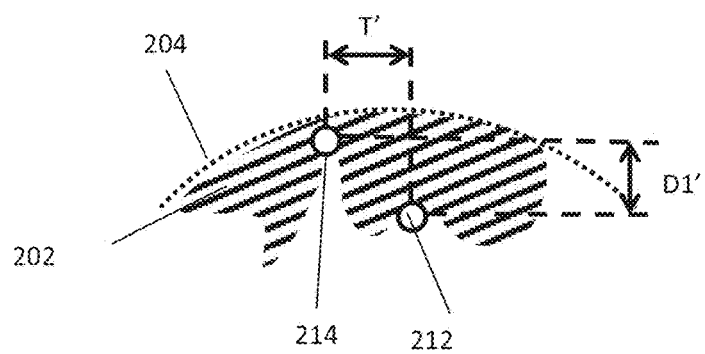
FIG. 2B is a simplified schematic cross sectional view of two portions of a device, within a vessel with an occlusion, after device expansion, according to some embodiments of the invention.

Referring now to FIGS. 2A-B: FIG. 2A is a simplified schematic cross sectional view of two portions 212, 214 of a device, within a vessel 204 with a clot 202, according to some embodiments of the invention.

Figure 6A:
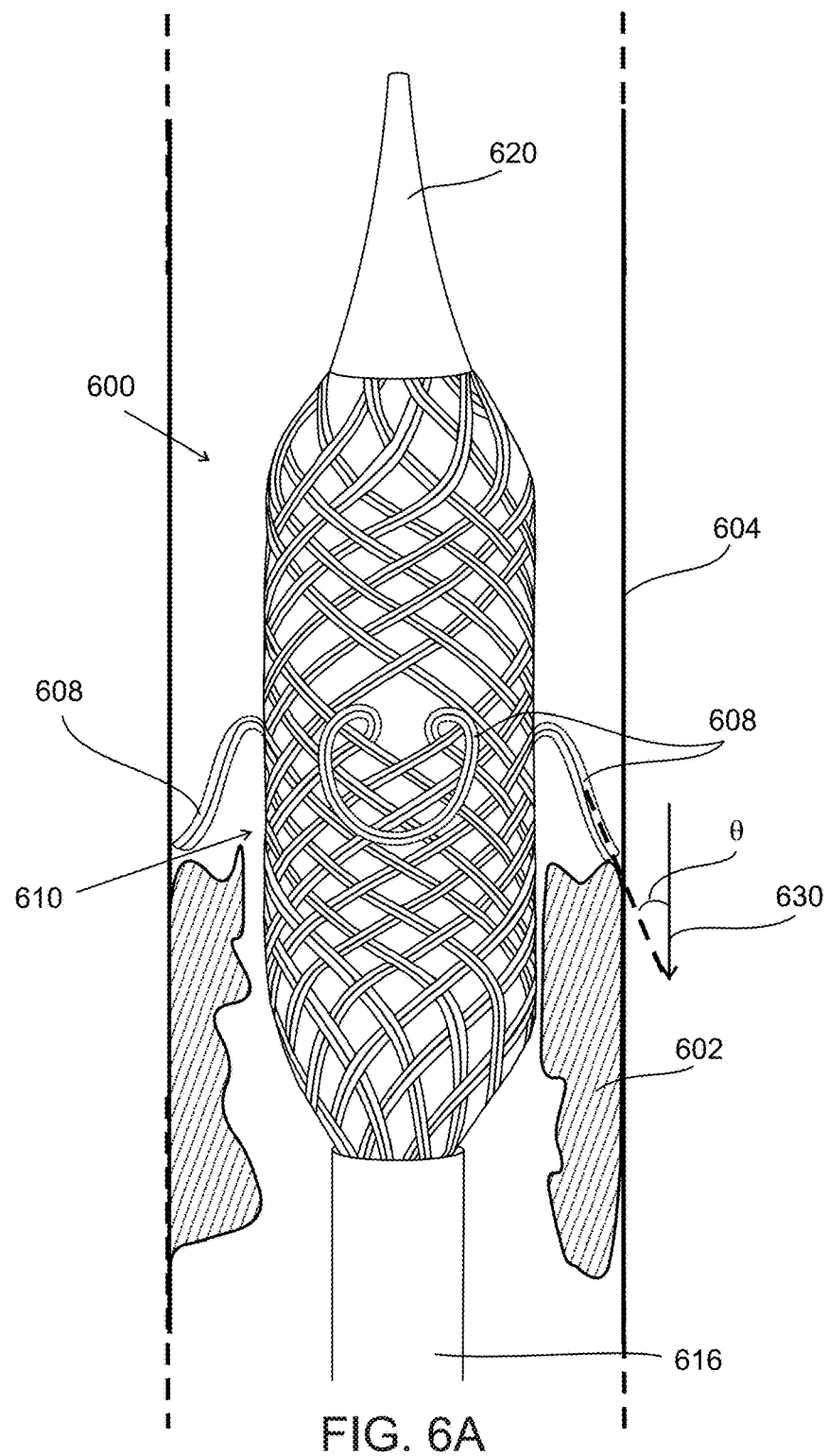
FIG. 6A is a simplified schematic side view of a device expanded within a blood vessel in the vicinity of clot material, according to some embodiments of the invention.

Examples of spaces within exemplary devices include:

FIG. 6A where a space is formed between protrusion 608 and portions of device body 610.

Figure 7A:
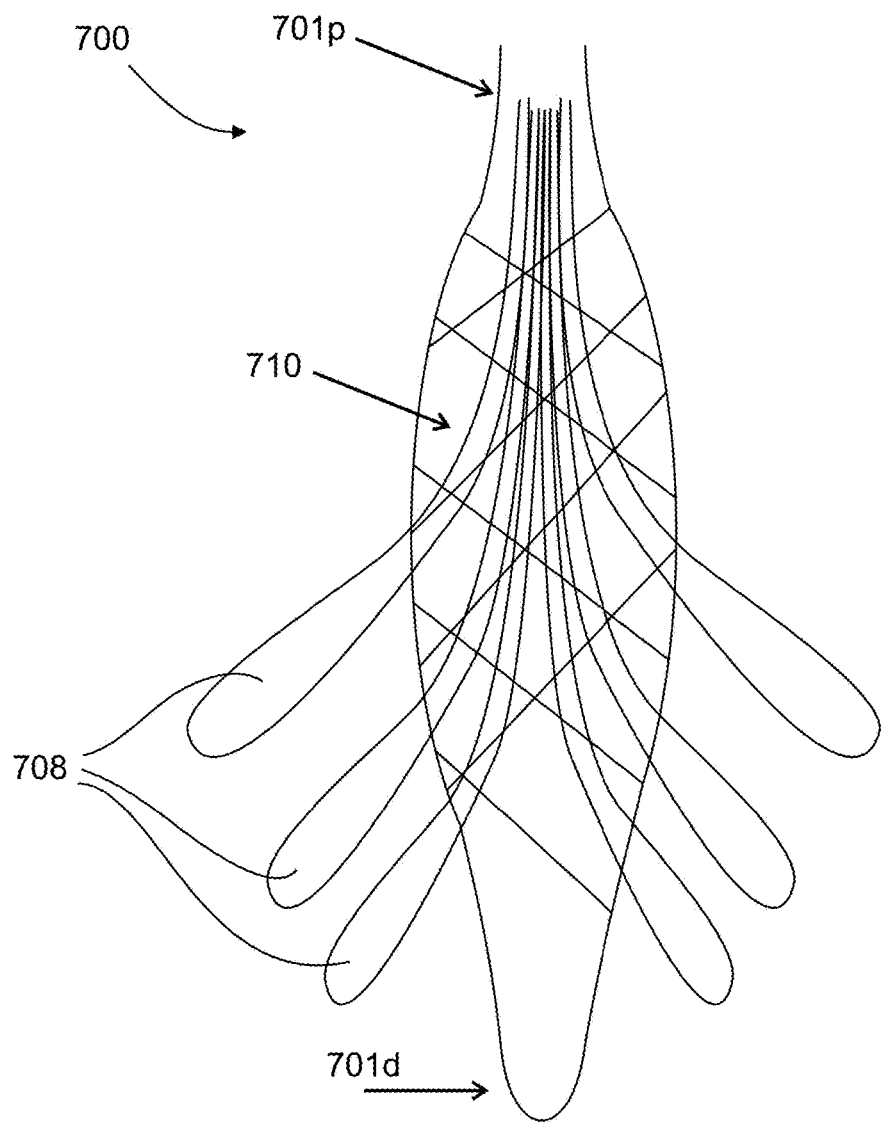
FIG. 7A is a simplified schematic side view of an expandable device including a plurality of protrusions, according to some embodiments of the invention.

FIG. 7A where spaces are formed within loops 708 and/or between loops 708 and/or between a loop and device body 710.

Figure 8A:
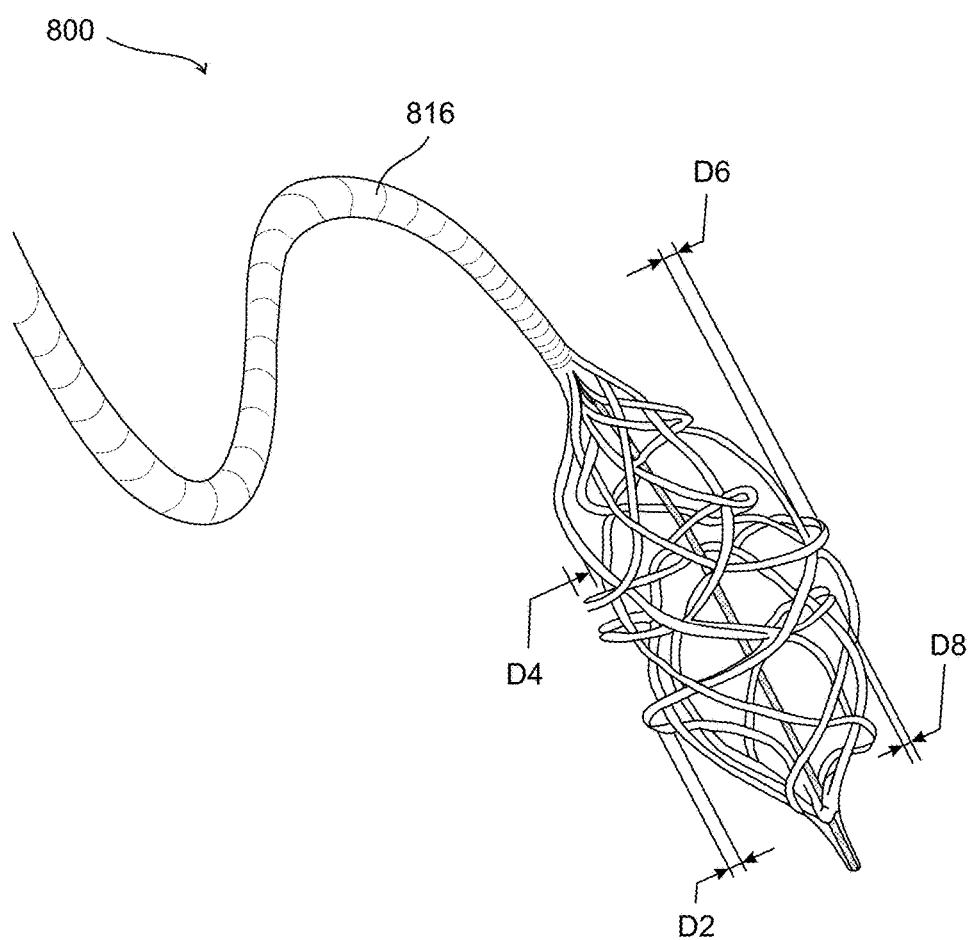
FIG. 8A is a simplified schematic side view of an expandable device, according to some embodiments of the invention.
Figure 8B:
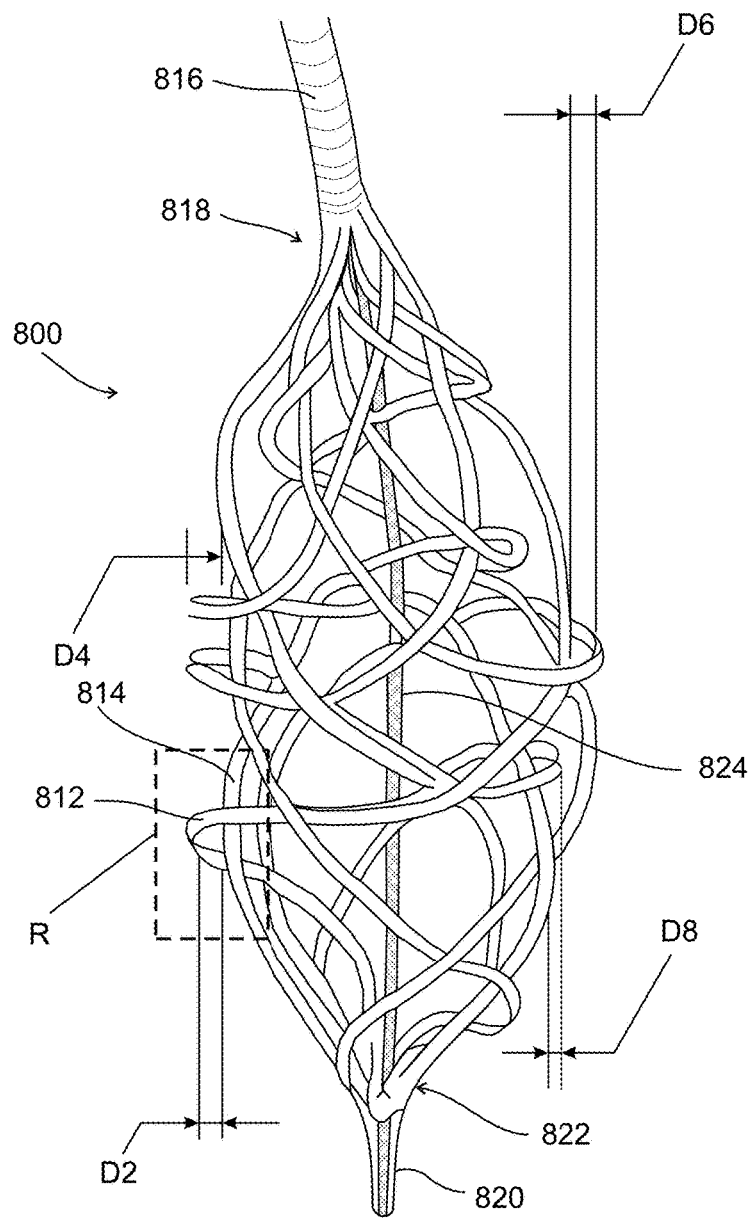
FIG. 8B is a simplified schematic side view of an expandable device, according to some embodiments of the invention.

FIG. 8B where a space is formed, for example, between wires 812 and 814.

Figure 2C:
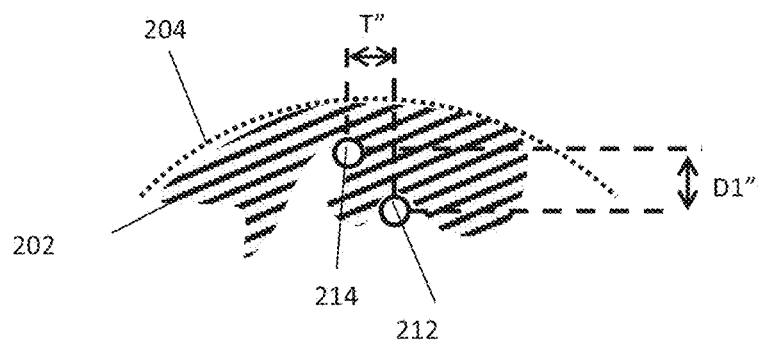
FIG. 2C is a simplified schematic cross sectional view of two portions of a device, within a vessel with an occlusion, after device contraction, according to some embodiments of the invention.

FIGS. 2A-C show a cross sectional view of the device where the section is taken perpendicular to a longitudinal axis of the device. Only part of vessel wall 204 is illustrated.

In some embodiments, expansion of the device causes an increase in separation between portions 212, 214 in one or more dimension. For example, in some embodiments, upon expansion of the device, a space between two portions of the device increases both in a direction perpendicular to the central longitudinal axis of the device and on a surface of the device (e.g. tangential and/or parallel to the central longitudinal axis).

In some embodiments, expansion of the device causes an increase in separation between portions 212, 214 in one dimension and a decrease in another dimension. For example, as described regarding FIGS. 12A-C.

FIG. 2B is a simplified schematic cross sectional view of two portions of a device, within a vessel with an occlusion, after device expansion, according to some embodiments of the invention. In an exemplary embodiment, expansion of the device increases the radial separation D' between portions 212, 1014: D'>D and/or tangential separation T1' of the portions, T1'>T1.

As mentioned previously, in some embodiments, inserting the device into obstructive material and/or positioning the device in proximity to obstructive material causes material to enter underneath one or more portion of the device: Referring now to FIG. 2A, in some embodiments, upon insertion of the device, clot material 202 enters into a space between two portions 212, 214 of the device (e.g. a wire pair). In some embodiments the portions 212, 214 are separated by one or more dimension. For example, as illustrated in FIG. 2A, in an exemplary embodiment, portions 212, 214 are separated axially (to a longitudinal axis of the device) by a distance D1 and are separated tangentially (to a longitudinal device axis) by distance T.

As mentioned previously, in some embodiments, (for example, after device expansion) the device is then contracted (e.g. partially contracted), reducing space/s into which clot material has entered in size (e.g. at least in one dimension), for example, trapping and/or holding the clot material under and/or between portions of the device. In some embodiments, the device is contracted before the device is removed and/or during removal of the device.

FIG. 2C is a simplified schematic cross sectional view of two portions of a device, within a vessel with an occlusion, after device contraction, according to some embodiments of the invention. In some embodiments, after contraction separation between portions is decreased in one or more dimensions, for example, T"<T' and/or D"<D'.

Although in FIG. 2C, the space between portions 212, 214 has reduced radially by movement of portion 214 away from vessel 204, in some embodiments, a radial size of the space is reduced, for example, pinching material between portions of the device, by, for example, moving portion 212 in the radial direction, while, for example, radial pressure of 214 upon obstructive material 202 is maintained.

In some embodiments, as is described elsewhere in more detail (e.g. FIGS. 12A-D expanding the device increases a radial space between two device portions whilst a dimension of the space between the portions in a different dimension (e.g. perpendicular to the radial direction) decreases. Movement of the portions, for example pinching obtrusive material within the space.

Figure 2D:
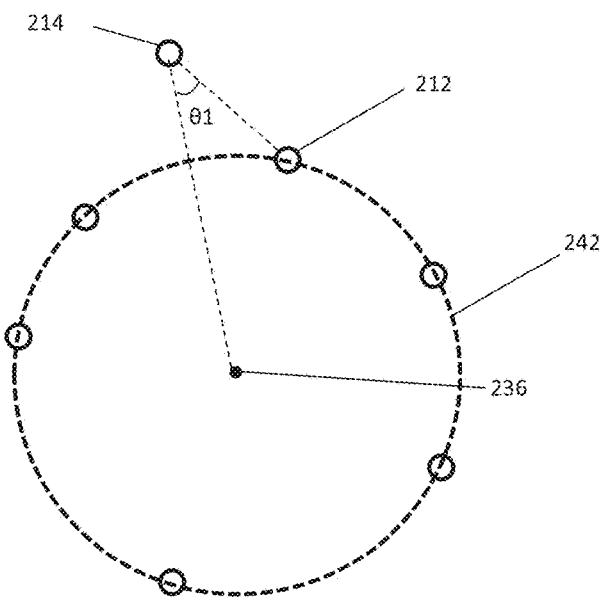
FIG. 2D is a simplified schematic cross sectional of a device including a protruding portion, according to some embodiments of the invention.

FIG. 2D is a simplified schematic cross sectional of a device 200 including a protruding portion 214, according to some embodiments of the invention.

In some embodiments, protruding portion 214 protrudes above a body of the device 242. The body of the device may be defined by the largest circular cross section 242 totally enclosed within device portions (illustrated as solid outlined circles in FIG. 2D and FIG. 2E).

In some embodiments, a space between protruding portion 214 and a nearest other portion of the device 212 includes a radial component: In some embodiments an angle, θ1 between a radial line extending from a central longitudinal point of the device 236 and a nearest portion of the device 212 to protruding portion 214 is less than 90°, or 5-89°, or 10-85°, or lower, or higher, or intermediate ranges or angles.

Figure 2E:
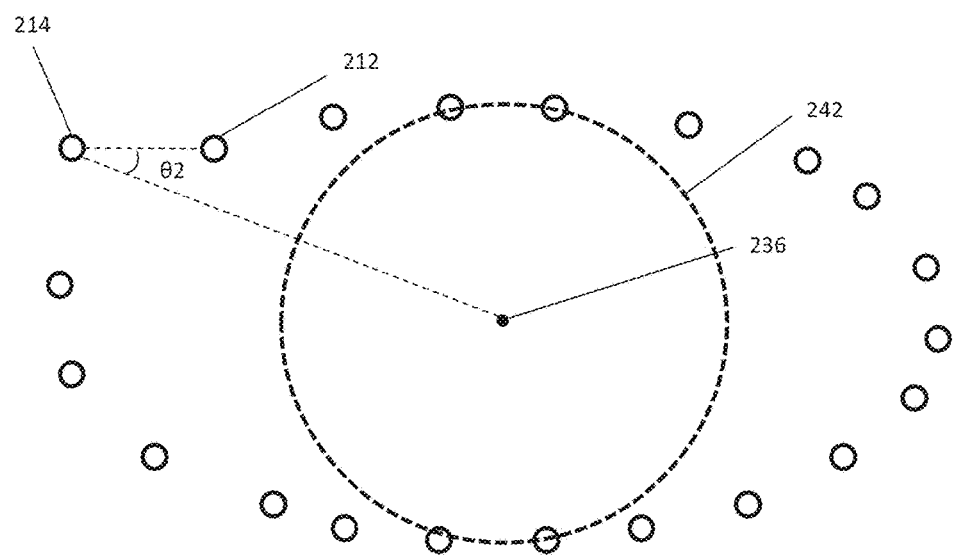
FIG. 2E is a simplified schematic a simplified schematic cross sectional of a device including a protruding portion, according to some embodiments of the invention.

In some embodiments, a longitudinal central axis of a (e.g. non-cylindrical) device is defined as the longitudinal central axis extending from the largest cylinder totally enclosed by the device. FIG. 2E is a simplified schematic a simplified schematic cross sectional of a device 200 including a protruding portion 214, according to some embodiments of the invention. In some embodiments, one or more portion of the device includes non-circular cross section, for example, the elliptical cross section as illustrated by FIG. 2E (device portions are illustrated by solid outlined circles). Circle 242 indicates a largest circular cross section enclosed by the device at this point, defining a central longitudinal point 236 (largest circular cross sections totally enclosed by the device defining longitudinal points define a central longitudinal axis).

In some embodiments, an angle, θ2 between a radial line extending from a central longitudinal point of the device 236 and a nearest portion of the device 212 to protruding portion 214 is less than 90°, or 5-89°, or 10-85°, or lower, or higher, or intermediate ranges or angles.

Exemplary Insertion and Expansion of a Device

In an exemplary embodiment, the occlusion is a blood clot obstructing a blood vessel.

Figure 3A:
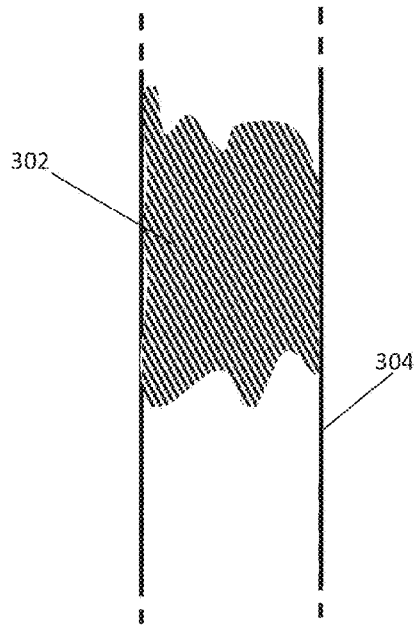
FIG. 3A is a simplified schematic section view of a clot in a blood vessel.

FIG. 3A is a simplified schematic section view of a clot 302 in a blood vessel 304. In some embodiments, clot 300 obstructs substantially all of a portion of the vessel (e.g. obstruction substantially fills the vessel cross section for at least a portion of the vessel).

Figure 3B:
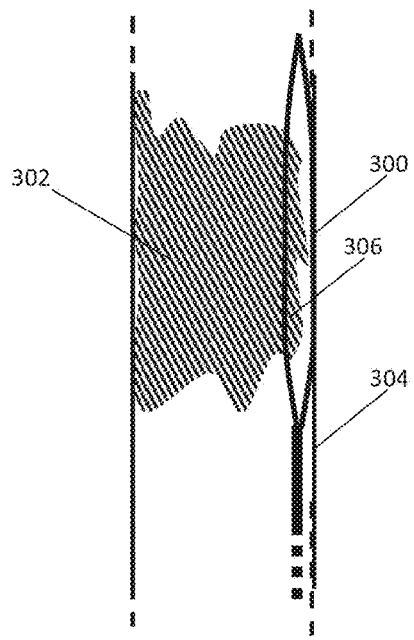
FIG. 3B is a simplified schematic section view of a clot in a blood vessel and a device delivered to a vicinity of the clot, according to some embodiments of the invention.

FIG. 3B is a simplified schematic section view of a clot 302 in a blood vessel 304 and an expandable device 300 delivered to a vicinity of the clot 302, according to some embodiments of the invention. In some embodiments, insertion of the device moves 300 at least a portion of clot e.g. displacing a portion of clot 302 from a vessel wall. In some embodiments, positioning of device 300 causes portions 306 of clot 302 to enter into device 300, for example into spaces within the device (e.g. radially underneath one or more protrusion and/or within one or more protrusion and/or within a body of the device).

Figure 3C:
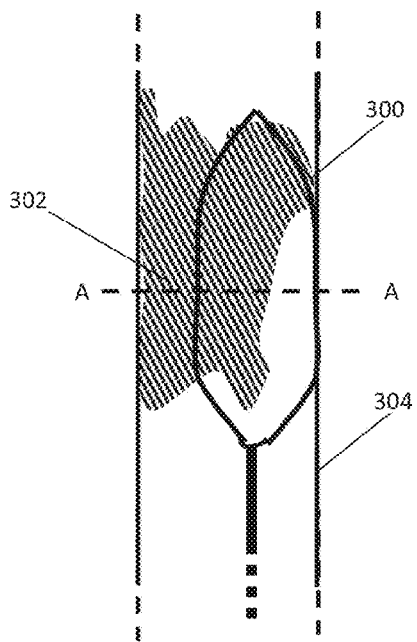
FIG. 3C is a simplified schematic section view of the device expanded within the vessel, capturing the clot, according to some embodiments of the invention.

In some embodiments, device 300 is expanded such that at least a portion of clot 302 enters into at least one space within device 300. FIG. 3C is a simplified schematic section view of the device 300 expanded within the vessel 304, capturing the clot 302, according to some embodiments of the invention.

Figure 3D:
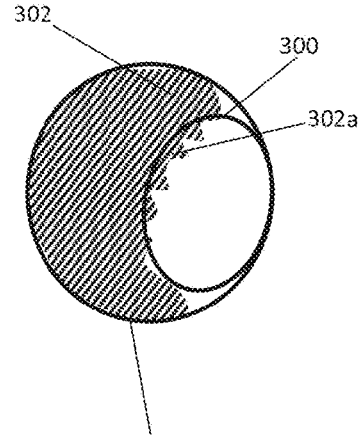
FIG. 3D is a cross sectional view, of a device expanded within a vessel at an axial location of a clot, where the section is taken perpendicular to a longitudinal axis of the device, according to some embodiments of the invention.

FIG. 3D is a cross sectional view, of a device 300 expanded within a vessel 303 at an axial location of a clot 302, where the section is taken perpendicular to a longitudinal axis of the device, according to some embodiments of the invention.

In some embodiments, FIG. 3D is a section taken at plane A-A as illustrated in FIG. 3C. In some embodiments, clot material 302a enters into at least one space within the expanded device 300.

Exemplary Removal of an Obstruction

As mentioned previously, in some embodiments, a device holds an obstruction (e.g. clot) against a vessel wall during removal of the obstruction, including where the vessel changes direction and/or dimension.

In some embodiments, one or more portion of the device (e.g. one or more protrusion) maintains sufficient outward force on obtrusive material between the device and vessel walls and/or the device holds obtrusive material within device space/s, optionally during changes to vessel geometry and size, such that the obtrusive material travels with the device through the vessel.

For example, in some embodiments, one or more protrusion (e.g. protrusions 608) maintain contact with vessel walls for a variety of vessel cross sectional areas.

Figure 4A:
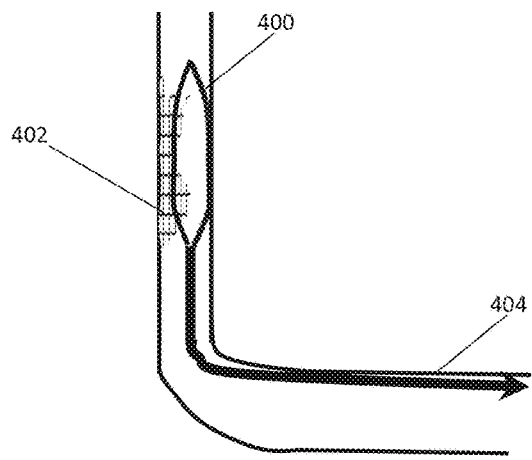
FIG. 4A is a simplified schematic side view of an expandable device for removal of clots, and a captured clot within a blood vessel, according to some embodiments of the invention.

FIG. 4A is a simplified schematic cross sectional view of an expandable device 400 and a captured clot 402 within a blood vessel 404, according to some embodiments of the invention.

Figure 4B:
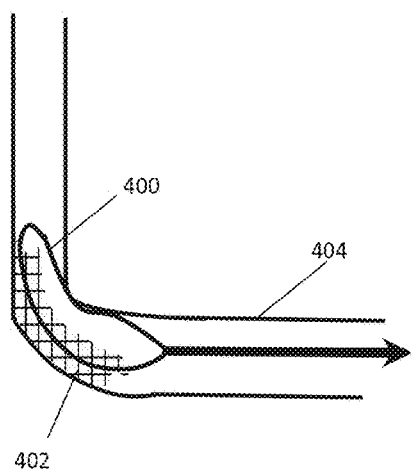
FIG. 4B is a simplified schematic side view of an expandable device removing a clot through a curve in a blood vessel, according to some embodiments of the invention.

FIG. 4B is a simplified schematic cross sectional view of an expandable device 400 removing a clot 402 through a curve in a blood vessel 404, according to some embodiments of the invention.

Figure 4C:
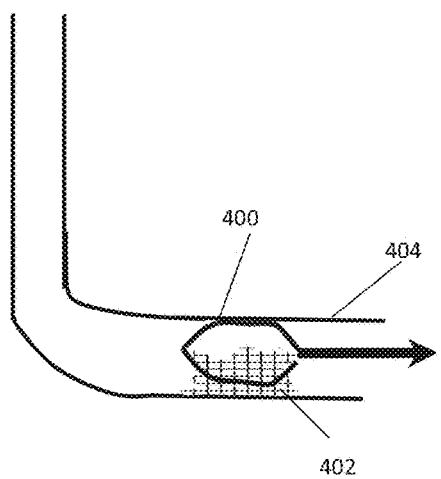
FIG. 4C is a simplified schematic side view of an expandable device removing a clot through an enlarged portion of a blood vessel, according to some embodiments of the invention.

FIG. 4C is a simplified schematic cross sectional view of an expandable device 400 removing a clot through an enlarged portion of a blood vessel 404, according to some embodiments of the invention.

Figure 4D:
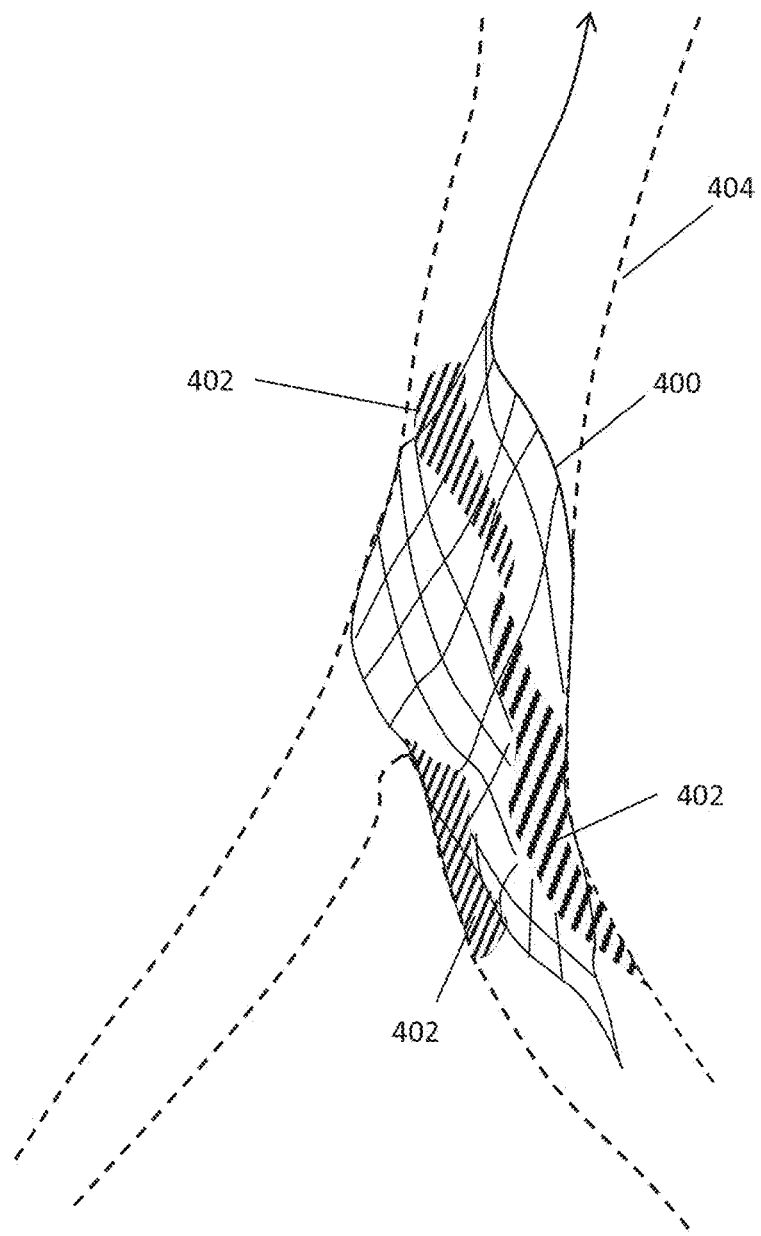
FIG. 4D is a simplified schematic cross sectional view of an expandable device navigating a curve and changes in cross sectional area of a blood vessel while removing clot material, according to some embodiments of the invention.

FIG. 4D is a simplified schematic cross sectional view of an expandable device 400 navigating a curve and changes in cross sectional area of a blood vessel 404 while removing clot material 402, according to some embodiments of the invention.

Exemplary Interaction of Insertion of Device with Obstruction

In some embodiments, insertion and/or positioning of the device places the device between an obstruction and a wall of the vessel (e.g. as illustrated in FIG. 3B and FIG. 3C).

In some embodiments, a device is inserted into an obstruction. In some embodiments, inserting the device into an obstruction pushes obstructive material away from the device. Additionally or alternatively, in some embodiments, inserting the device into an obstruction causes some of the obstructive material to enter into device space/s (e.g. radially underneath one or more protrusion and/or within one or more protrusion and/or within a body (e.g. 610, 810) of the device). In some embodiments, obstructive material at least partially coats walls of the vessel, for example as illustrated by FIG. 6A.

Figure 5A:
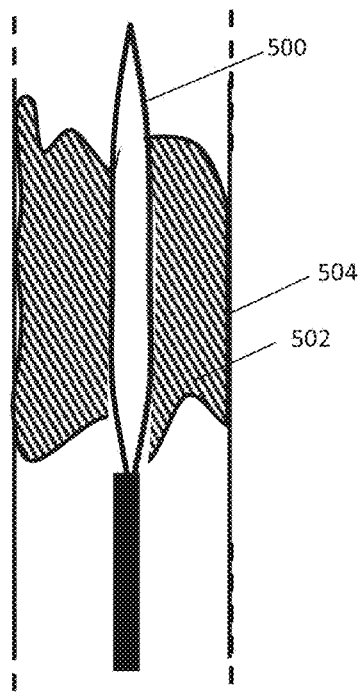
FIG. 5A is a simplified schematic cross sectional view of an expandable device delivered to a vicinity of a clot within a blood vessel, according to some embodiments of the invention.

FIG. 5A is a simplified schematic cross sectional view of an expandable device 500 delivered to in proximity of a clot 502 within a blood vessel 504, according to some embodiments of the invention.

Figure 5B:
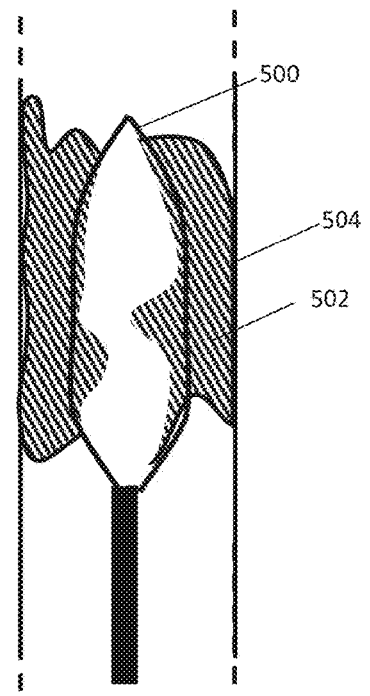
FIG. 5B is a simplified schematic cross sectional view of the device of FIG. 5A expanded to capture the clot, according to some embodiments of the invention.

FIG. 5B is a simplified schematic cross sectional view of the device of FIG. 5A expanded to capture the clot 504, according to some embodiments of the invention.

Exemplary Devices

FIG. 6A is a simplified schematic side view of a device 600 expanded within a blood vessel 604 in the vicinity of obstruction 602, according to some embodiments of the invention.

In an exemplary embodiment (e.g. as illustrated in FIG. 6A), a device (e.g. under uniform external pressure) includes a central portion with a cylindrical outer shape and end portions with tapered outer shapes.

Alternatively or additionally, in some embodiments, the device includes an oval cross section portion (e.g. a central portion). Alternatively or additionally, in some embodiments, the device includes an irregular shape.

In some embodiments, device 600 includes an expandable structure formed of plurality of wires, where one or more of the wires are coupled at a different radial position at a distal and a proximal end of the structure.

Figure 6B:
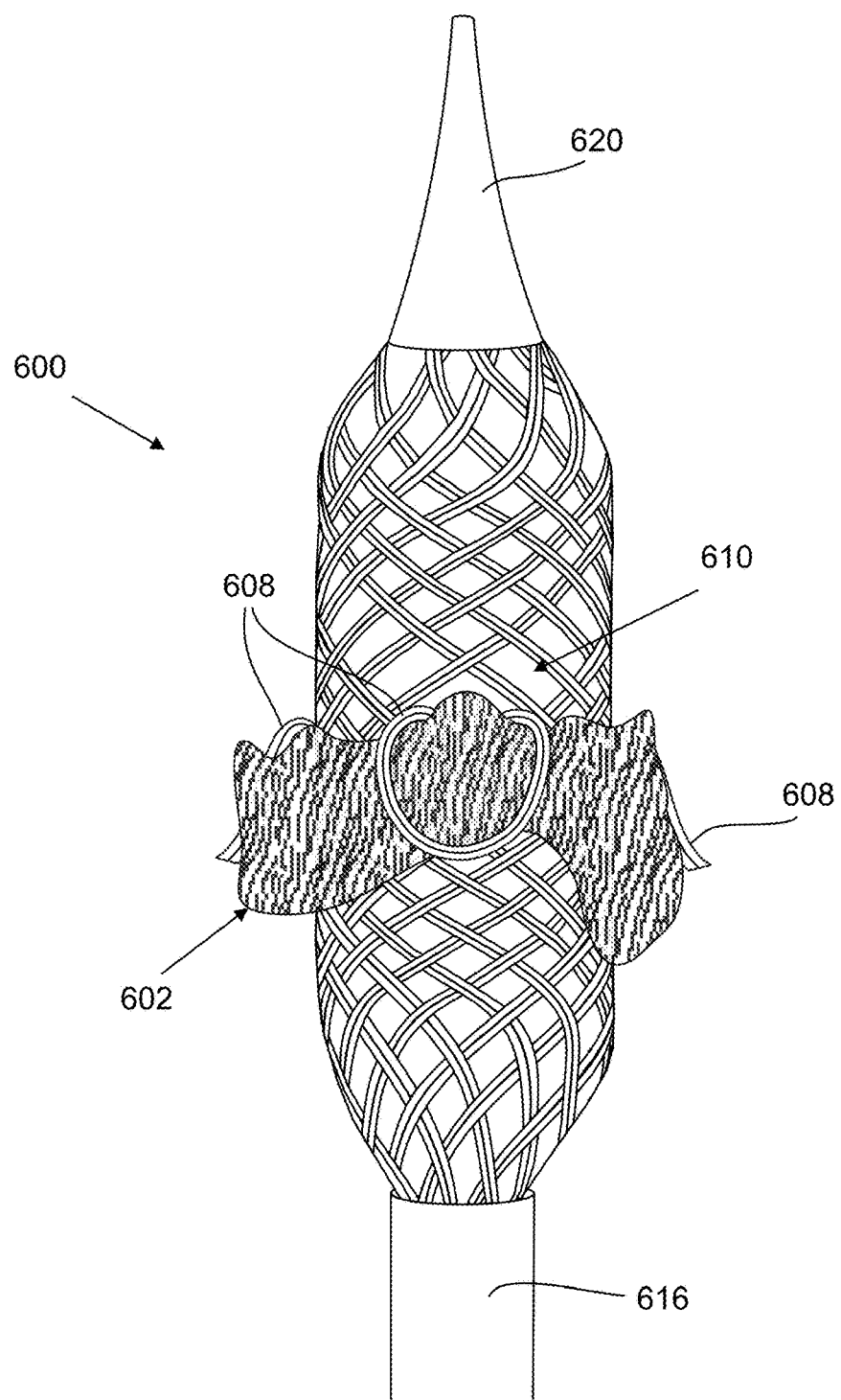
FIG. 6B illustrates clot material captured underneath protrusions, for example, between protrusions and device body, according to some embodiments of the invention.

In some embodiments, a device includes wires which transverse a path which includes changes in radial position (e.g. angle from a central longitudinal axis to the position) of the wire (e.g. a helical path) from the distal end to the proximal end of the device. In some embodiments, an individual wire passes over some other wires which it crosses along its path and under others. In an exemplary embodiment, e.g. as illustrated in FIGS. 6A-B, wires alternatively pass under and over consecutive wires in their path, e.g. forming a mesh.

In some embodiments, one or more wire is connected to one or more other wire connected at the wire distal and/or proximal ends. In some embodiments, wires are connected, for example, by welding and/or gluing together.

In some embodiments, the wires are connected at one or more end by one or more element. For example, in some embodiments, the wires are coupled at a proximal end to an elongated element 616 which by which a user applies force to the device (pushing and/or pulling the device by applying force to the elongated element. In some embodiments, wires are coupled at an expandable structure distal end by a capping end portion 620.

In some embodiments, more than one wire extending from the proximal to distal end is formed from a single wire which transverses a path traversing distal to proximal ends more than once.

In some embodiments, wires forming the device form a tubular shaped mesh surface, a body of the device 610 between the distal and proximal ends.

In some embodiments, the expandable structure is expanded by reducing a longitudinal distance between end portion 620 and elongated element 616, for example, using an element connected end portion 620 (e.g. as described regarding element 824 connected to end portion 820 in FIG. 8B).

Exemplary Protrusions

In some embodiments, a device (e.g. 600, 700, 800) includes one or more protruding portion (e.g. 608, 708, 812) under which (e.g. as described previously) clot material is captured.

In some embodiments, protruding portions (e.g. 608) remain protruding as the device is removed, for example, not flattening and/or folding backwards (e.g. against device body 610). In some embodiments, protruding portion/s are constructed from wires selected to be sufficiently strong to remain protruding as the device is removed. For example, in some embodiments protruding portion/s are constructed of wire with cross sectional dimensions (e.g. as quantified below), where the cross sectional dimension is selected to provide sufficient resistive force and/or moment of inertia.

In some embodiments, protrusion/s exert outwards (e.g. elastic) force on the vessel, potentially maintaining contact between the protrusion/s and vessel walls through changes in vessel cross sectional dimension. In an exemplary embodiment, an elastically relaxed cross sectional dimension of the device including the protrusions is larger than the largest vessel through which the device travels in order to remove the clot (for example, protrusions maintain elastic force on obstructive material and/or vessel walls, and do not relax elastically during the device's removal of the obtrusive material and/or during removal of the device).

In an exemplary embodiment, protruding portions 608 are rounded, potentially reducing risk of damage (e.g. to vessels walls) during use of the device e.g. when the device is expanded into and/or moved past the vessel walls.

In some embodiments, a rounded protrusion includes a tip (a portion which protrudes most radially) where a width of the tip is at least 20%, or at least 30%, or at least 40%, of a length of the protrusion, where the length of the protrusion is measured as the axial length of the wire from where it extends radially from the device body.

Exemplary Angle of Protrusions with Respect to Device Body

In some embodiments, one or more protrusion is angled where a distal contour of the protrusion has an acute angle θ to a direction of removal 630 of the device.

In some embodiments, during expansion of device 600 angle θ increases, increasing an axial space underneath protrusions 608. In some embodiments, during contraction of device 600, angle θ decreases, potentially holding clot material.

In some embodiments, protrusion/s are angled to capture clot material during movement of the device, for example, one or more protrusion is angled at an acute angle to a central axis and/or direction of movement of the device.

Exemplary Loop Protrusions

In some embodiments, one or more protruding portion is a loop structure, (e.g. 608, 708). For example, where a wire forming the loop includes distal and proximal ends which are both connected to the device proximal or distal end. For example, the device illustrated by FIG. 6A includes protrusions 608 where the protrusion is formed by a wire connected at both ends to elongated component 616.

In some embodiments, loop ends are connected to different portions of the device.

In some embodiments, wires forming protruding portion/s follow a path which departs from and return to a tubular expandable device surface. In some embodiments, (e.g. as described elsewhere) the wire forming a protrusion extends radially away from the tubular surface 610, in some embodiments the wire also extends along the device in a longitudinal direction.

Exemplary Protrusions Forming an Integral Portion of the Device

In some embodiments, a protruding portion forms an integral part of the device. For example, as illustrated in FIG. 6A, in some embodiments protruding portions 608 are formed from wires which also form a part of a device body 610.

In some embodiments, one or more protrusion is constructed from a wire extending around and/or along the device (e.g. around 10-90%, 50-80% of a device circumference and/or along 10-90% or 50-80% of a length of the device). For example, wires forming protrusions 608 include portion/s which follow a path around the tubular expandable device body 610.

In some embodiments, a protrusion is formed by a wire which is directly coupled to an elongated portion (e.g. protrusion 608 connected to elongated component 616) by which force (e.g. pulling) is applied to the expandable device.

Potentially, a protrusion forming an integral part of the device transfers force applied to the device more effectively, for example for applying force to the clot (e.g. in order to move the clot).

Exemplary Location of Protrusions

In some embodiments, multiple protrusions 608 are disposed each at a different radial angle from a central longitudinal axis of the device, the protrusions potentially able to remove obstructive material from different areas of the vessel wall. In some embodiments, multiple protrusions disposed at different radial angles allow a device to be inserted at a range of rotational orientations between a vessel wall and for one or more protrusion to interact with the obstruction, e.g. the device operation is potentially insensitive to rotational positioning with respect to the obstruction.

In an exemplary embodiment, device 600 includes four protrusions, disposed with centers of the protrusions separated by 90° when viewing protrusion location at an angle perpendicular to a longitudinal central axis of the device. In an exemplary embodiment, multiple protrusions are approximately the same in size and protrude approximately to the same extent (given equivalent pressures on each protrusion). In an exemplary embodiment, a center of where each protrusion meets a surface of device body 610 forms a plane perpendicular to a longitudinal axis of the device.

FIG. 6B illustrates clot material 602 captured underneath protrusions 608, for example, between protrusions 608 and device body 610.

In some embodiments, protrusions vary in size and/or orientation and/or axial position on the device.

FIG. 7A is a simplified schematic side view of an expandable device 700 including a plurality of protrusions 708, according to some embodiments of the invention. In some embodiments, protrusions 708 are dispersed along a longitudinal axis of device 700.

In some embodiments, expandable structure 700 includes a plurality of wires connected between a distal 701d and proximal 701p ends of the structure. In some embodiments (e.g. as described regarding FIG. 6A), a plurality of wires form a tubular mesh.

In some embodiments, protrusions are formed by loops 708 of wires extending from and returning to proximal end 701p. In some embodiments, loops 708 follow a path through tubular mesh 710 (loops pass inside tubular mesh 710) and protrude through gaps in tubular mesh. Where, in some embodiments, each loop protrudes through the mesh at a different position on the mesh e.g. each loop protruding at a radial and longitudinal position on the mesh e.g. a unique radial and/or longitudinal position on the mesh.

Figure 7B:
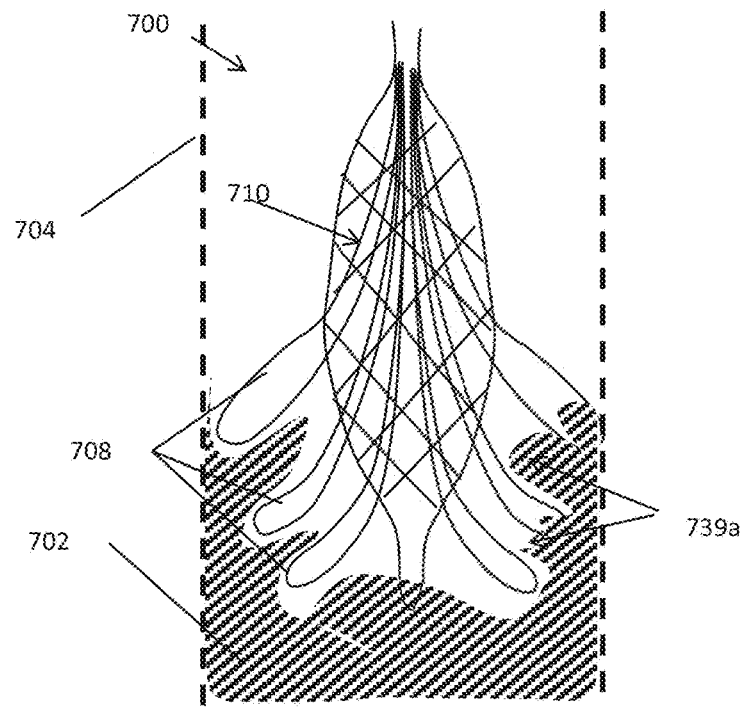
FIG. 7B is a simplified side view of an expanded device within a vessel, according to some embodiments of the invention.

FIG. 7B is a simplified side view of an expanded device 700 within a vessel 704, according to some embodiments of the invention.

Figure 7C:
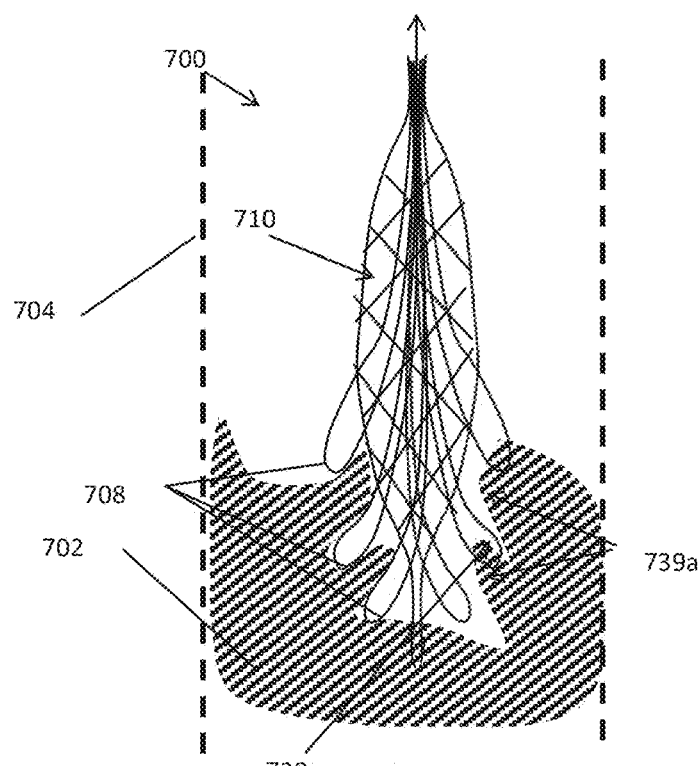
FIG. 7C is a simplified side view of a contracted device within a vessel, according to some embodiments of the invention.

FIG. 7C is a simplified side view of a contracted device 700 within a vessel 704, according to some embodiments of the invention.

Figure 7D:
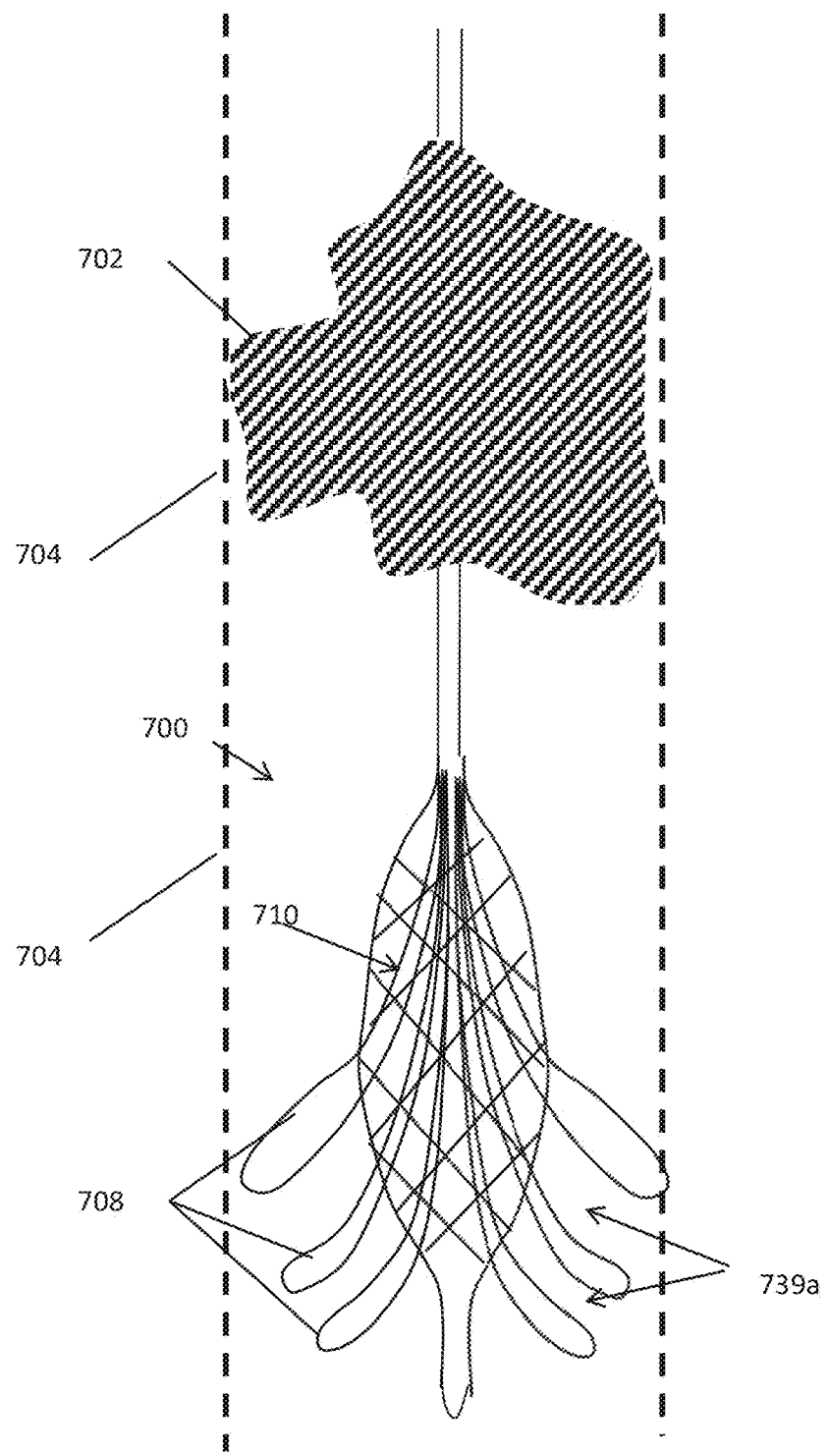
FIG. 7D is a simplified side simplified side view of an expanded device, which has been inserted through obstructive material within a vessel, according to some embodiments of the invention.

FIG. 7D is a simplified side simplified side view of an expanded device 700, which has been inserted through obstructive material 702 within a vessel 704, according to some embodiments of the invention. As mentioned previously, in some embodiments, a device is pushed through and/or past an occlusion, then expanded and then pulled past the occlusion, removing (e.g. "raking") the occlusive material 702 away from its' original position within vessel 704.

Figure 7E:
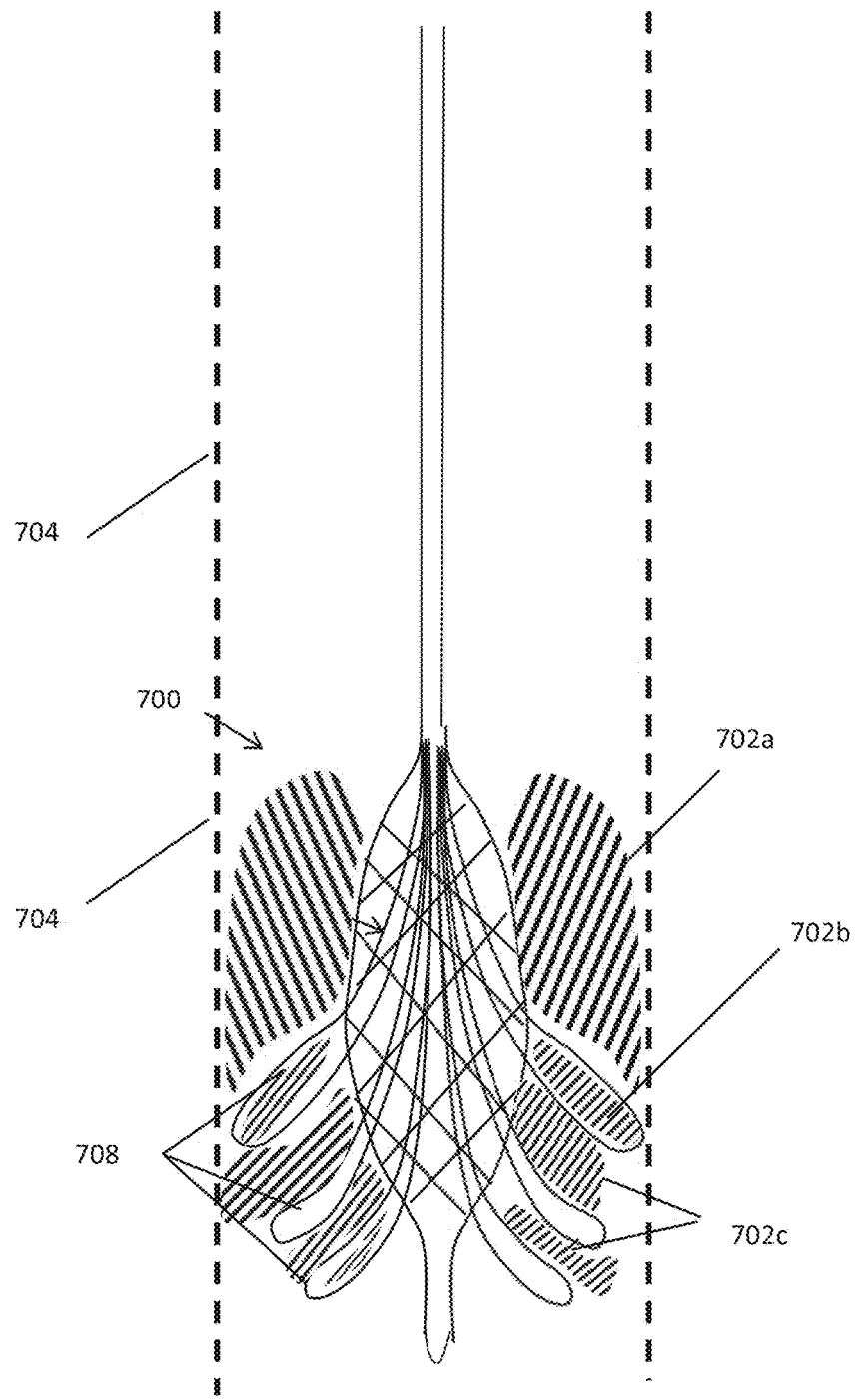
FIG. 7E is a simplified side view of an expanded device, which has been pulled past obstructive material within a vessel, according to some embodiments of the invention.

FIG. 7E is a simplified side vie of an expanded device 700, which has been pulled past obstructive material within a vessel 704, according to some embodiments of the invention. In some embodiments, obstructive material enters into loops 702b and/or between loops 702c. In some embodiments, obstructive material 702a located between device 700 and vessel walls is moved and/or removed by pulling the device through vessel 704.

As mentioned previously, optionally, in some embodiments, loops 708 exert outwards force (e.g. elastic force) on the obstructive material and/or vessel walls.

In some embodiments, during and/or after expansion of the device clot material 702 enters into spaces 739 between protrusions 708. In some embodiments, contraction of the device, reduces space/s (e.g. spaces 739a are larger than spaces 739b) between protrusions, in at least one dimension and, in some embodiments, reduces space/s between protrusions in a radial direction.

In some embodiments, during and/or after expansion of the device clot material 702 enters into space/s 738 within protrusions. In some embodiments, during and/or after expansion of the device, a space within a protrusion is increased in size and/or in one or more dimension and/or in a radial direction. Conversely, in some embodiments, during contraction and/or removal of the device, a space within a protrusion is decreased in size, in one or more dimension and/or in a radial direction.

Exemplary Device Including Wire Pair Protruding Portions

FIG. 8A is a simplified schematic side view of an expandable device 800, according to some embodiments of the invention. FIG. 8B is a simplified schematic side view of an expandable device 800, according to some embodiments of the invention.

Referring now to FIG. 8B, which is an enlarged view of a portion of the device illustrated in FIG. 8A:

In some embodiments, device 800 (e.g. under uniform pressure) has an outer surface of the device with a narrow distal end which broadens towards a longitudinally central portion of the device, the outer surface of the device then narrowing towards a proximal end of the device.

In an exemplary embodiment, device 800 includes an elongate element 816 attached to a body of the device, for example, for moving device 800 within a vessel. In some embodiments, a device elongate element (e.g. 816, 616, 716) is flexible. In some embodiments, a first end 818 of wires making up the device are connected to elongate element 816.

In some embodiments, device 800 includes an end portion 820 to which a second end of wires 822 are attached. In some embodiments, a control portion 824 (e.g. a wire) is attached to end portion 822 and passes through the device and optionally through a hollow portion of elongate element 816. In some embodiments, geometry of device 800 is changed by retracting (e.g. pulling) control wire 824 through elongate element 816. In some embodiments, control wire 824 follows a central longitudinal axis of the device.

In some embodiments, retracting control wire 824 through elongate element expands an average cross sectional area of the device and reduces a longitudinal length of the device.

In some embodiments, end portion 820 is where two or more device wires are connected to each other (e.g. by welding). In some embodiments, wires follow a path from elongate element 816 to end portion 820 where each wire passes under and/or over at least one other wire. In some embodiments, one or more wire connected between end portion 820 and elongate element 816 has a longer length that one or more other wire, and, in some embodiments, the wire forms a protrusion (e.g. wire 812). In some embodiments, one or more wire is shaped (e.g. by heat treatment e.g. as described herein) to have a shape including a protrusion.

Exemplary Wire Pairs

In some embodiments, a device 800 includes one or more wire pair, where the wire pair includes, at least under some levels of expansion of the device, a separation, for example, separations D2, D4, D6, D8.

Referring to an exemplary wire pair and separation, separation D2 is between wires 812 and 814.

Figure 9A:
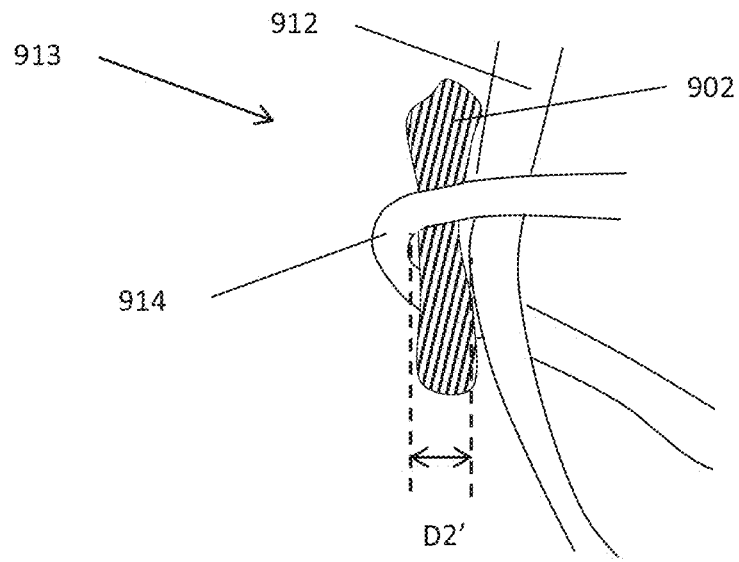
FIG. 9A is a simplified schematic side view of a wire pair capturing clot material, according to some embodiments, of the invention.
Figure 9B:
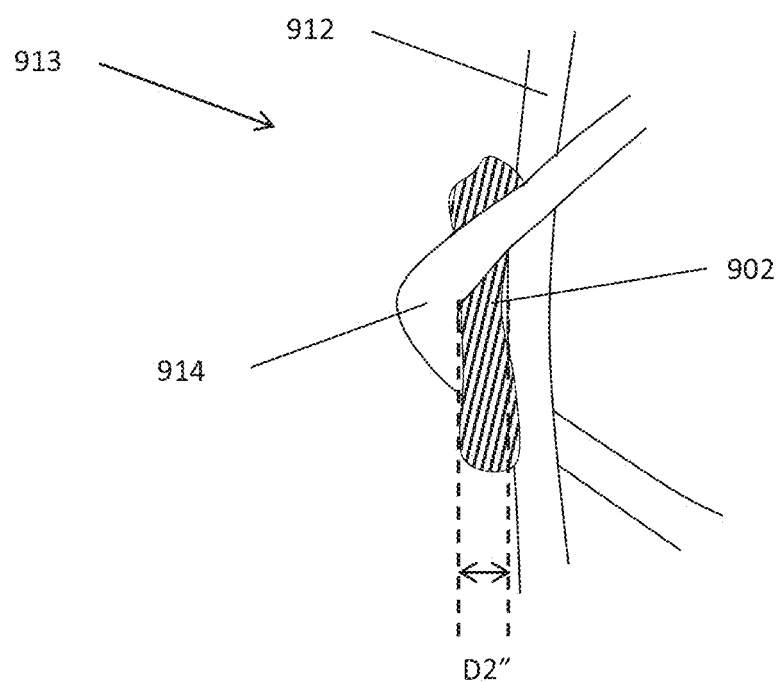
FIG. 9B is a simplified schematic side view of a wire pair capturing clot material, according to some embodiments, of the invention.

FIG. 9A and FIG. 9B illustrate an enlarged view of a device wire pair, for example, a portion of a wire pair illustrated within region R of FIG. 8B.

FIG. 9A is a simplified schematic side view of a wire pair 912, 914 capturing clot material, according to some embodiments, of the invention.

FIG. 9B is a simplified schematic side view of a wire pair 912, 914 capturing clot material, according to some embodiments, of the invention.

In some embodiments, FIG. 9B illustrates the wire pair of FIG. 9B after the device (e.g. device 800) has been reduced in cross sectional area (e.g. by advancing control wire 824). In some embodiments, a separation between the wires 912, 914 of the wire pair is reduced; D2"<D'. In some embodiments, reduction in the separation is associated with reduction in curvature of wires 912 and/or 914.

Exemplary Coupling of Obstructive Material to the Device, Interwoven Portion/s

In some embodiments, clot material is captured within a mesh device portion.

In some embodiments, clot material is captured by a portion of the device including interwoven portions (also herein termed "mesh"), for example, one or more portion following a path where it lies under portion/s and over portion/s (e.g. under and over referring to a radial direction).

Figure 10:
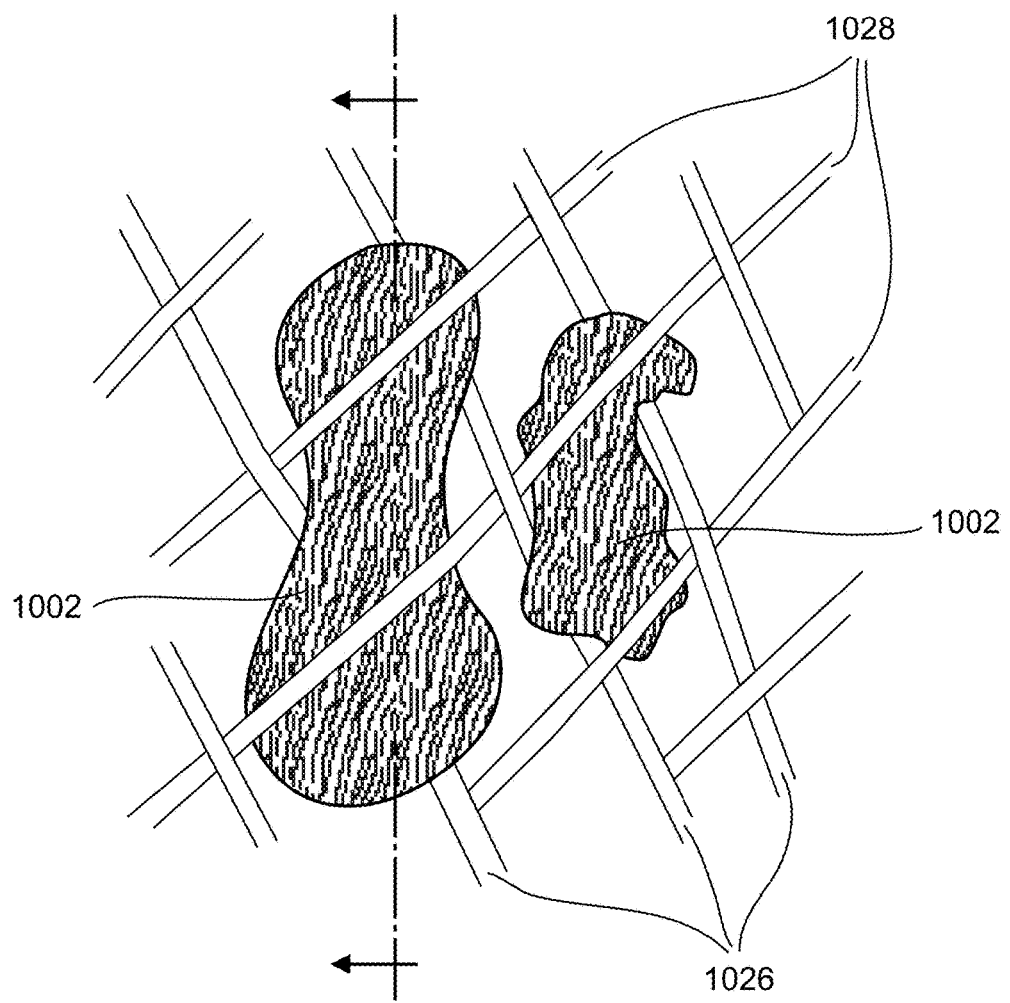
FIG. 10 is a simplified schematic top view of clot material captured within a mesh device portion, according to some embodiments of the invention.

FIG. 10 is a simplified schematic top view of clot material 1002 material captured within a mesh device portion, according to some embodiments of the invention.

In some embodiments, at least a portion of a device includes a mesh structure where one or more wire interweaves with other wires, for example, passing over some wires and under other wires. In an exemplary embodiment, the device includes warp 1026 and weft wires 1028 which are, for example, evenly spaced.

In some embodiments, crossings of (also herein termed junctions between) warp and weft wires form wire pairs (e.g. as described previously).

Figure 11:
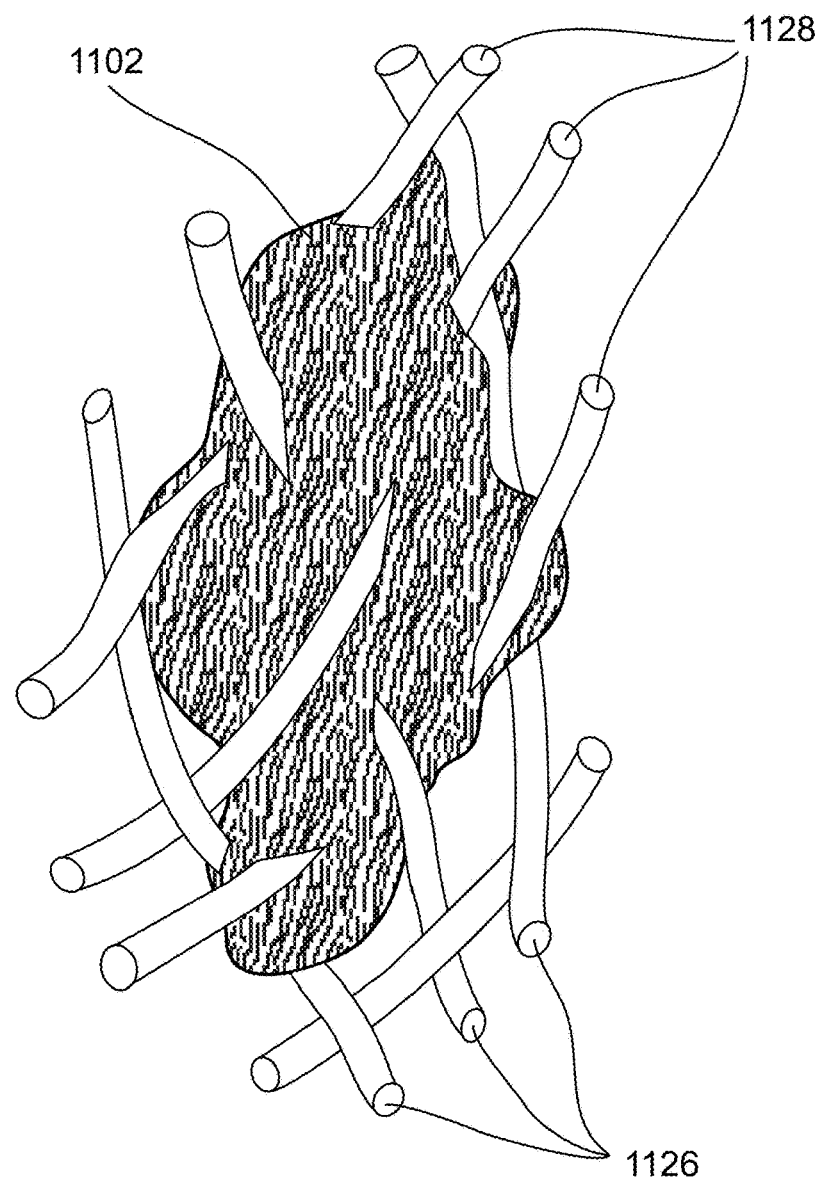
FIG. 11 is a simplified schematic top view of clot material captured within a mesh device portion, according to some embodiments of the invention.

FIG. 11 is a simplified schematic top view of obstructive material captured within a mesh device portion, according to some embodiments of the invention. In some embodiments, obstructive material within the device distorts the device structure, e.g. due to hardness of the obstructive material.

Figure 12A:
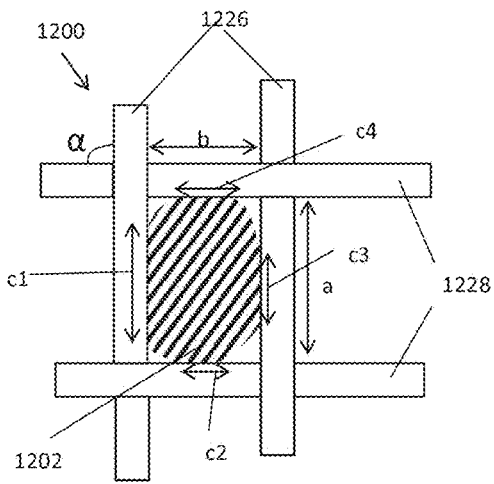
FIG. 12A is a simplified schematic top view of a clot material and a mesh device portion, according to some embodiments of the invention.

FIG. 12A is a simplified schematic top view of a clot material 1202 and a mesh device portion 1200, according to some embodiments of the invention. In some embodiments, contact between clot material 1202 and the device (contact lengths c1, c2, c3 and c4) is partial, for example with clot material 1202 contacting 5-95%, or 10-90%, or 50-80%, or lower or higher or intermediate ranges or percentages of a length of a warp wire between weft wires (a) and/or of a length of weft wires between warp (b) wires. For example, c1/a×100%=50-90%.

Figure 12B:
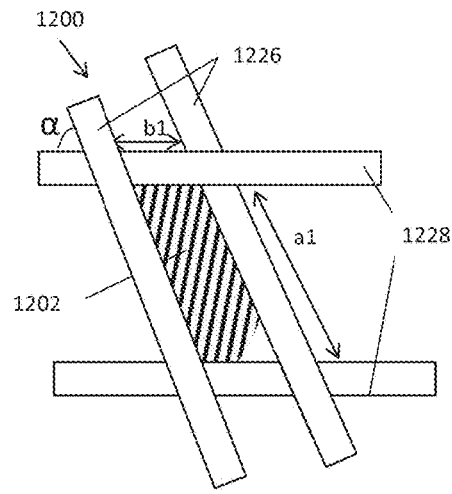
FIG. 12B is a simplified schematic top view of the device portion of, after device expansion, according to some embodiments of the invention.

In some embodiments, expansion of the device changes an angle between one set of wires (e.g. warp wires) and another set of wires (e.g. weft wires). FIG. 12B is a simplified schematic top view of the device portion of 12A, after device expansion, according to some embodiments of the invention. In some embodiments, an angle between warp and weft wires changes during device expansion, for example, from 90° in FIG. 12A to 45° in FIG. 12A.

In some embodiments, a change in angle α, between warp and weft wired during expansion is 10-90°, or 20-70°, or 40-50°, or smaller, or larger, or intermediate angle changes.

In some embodiments, a device includes a range for angle α, for example, corresponding to different levels of expansion of the device, of 5-175°, or 10-165°, or 45-110° or lower or higher or intermediate ranges or angles.

In some embodiments, concurrent reduction of the space in one dimension (e.g. radially between warp and weft wires) and increase in the space in another dimension increases (in the plane of warp and weft wires, as shown in FIGS. 12A-B), the structure potentially concurrently accepting and trapping clot material.

Figure 12C:
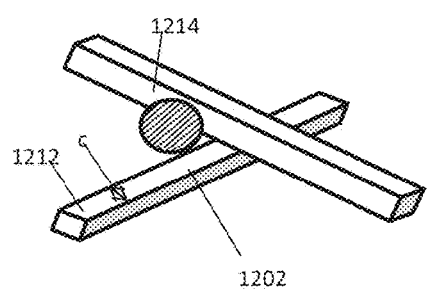
FIG. 12C and FIG. 12D show a side view of trapping of clot material, as the device is expanded, between a warp and weft wire, according to some embodiments of the invention.
Figure 12D:
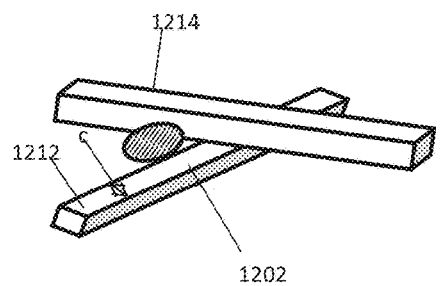

FIG. 12C and FIG. 12D show a side view of trapping of clot material, as the device is expanded, between a warp 1212 and weft wire 1214, according to some embodiments of the invention.

Figure 12E:
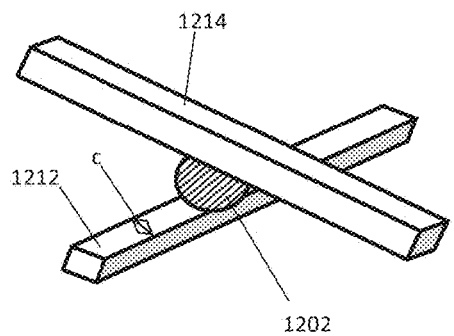
FIG. 12E is a simplified schematic side view of clot material between wires, according to some embodiments of the invention.

In some embodiments, clot material is between crossing portions of the device, e.g. where a warp wire passes over a weft wire. FIG. 12E is a simplified schematic side view of clot material 1202 between wires 1212, 1214, according to some embodiments of the invention. In some embodiment, clot material 1202 contacts 5-95%, or 10-90%, or 50-80% %, or lower or higher or intermediate ranges or percentages of a length of a portion underneath another portion, e.g. length c as illustrated in FIG. 12B.

Exemplary Wire Pairs Including Connections

In some embodiments, two or more wires between which a space is generated and/or enlarged are connected at two or more points. In some embodiments, a length of a first wire between two points is longer than a length of a second wire connected to the same two points. Reducing a distance between the two connections, in some embodiments, increases a distance (e.g. a space in at least one dimension) between the two wires.

Figure 13A:
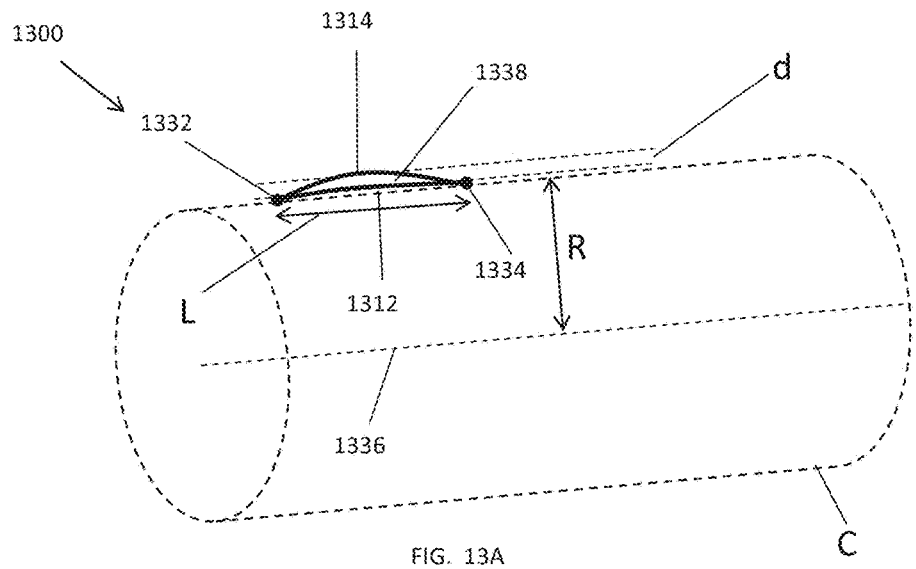
FIG. 13A is a simplified schematic side view of an expandable device including a wire pair with connections between wires, according to some embodiments of the invention.

FIG. 13A is a simplified schematic side view of an expandable device 1300 including a wire pair including junctions 1332, 1334 between wires 1312, 1314, according to some embodiments of the invention.

In some embodiments, one or more of junctions 1332, 1334 is a connection between wires 1312, 1314. In some embodiments, one or more of junctions 1332, 1334 is a point where one wire passes over and/or around another wire.

Figure 13B:
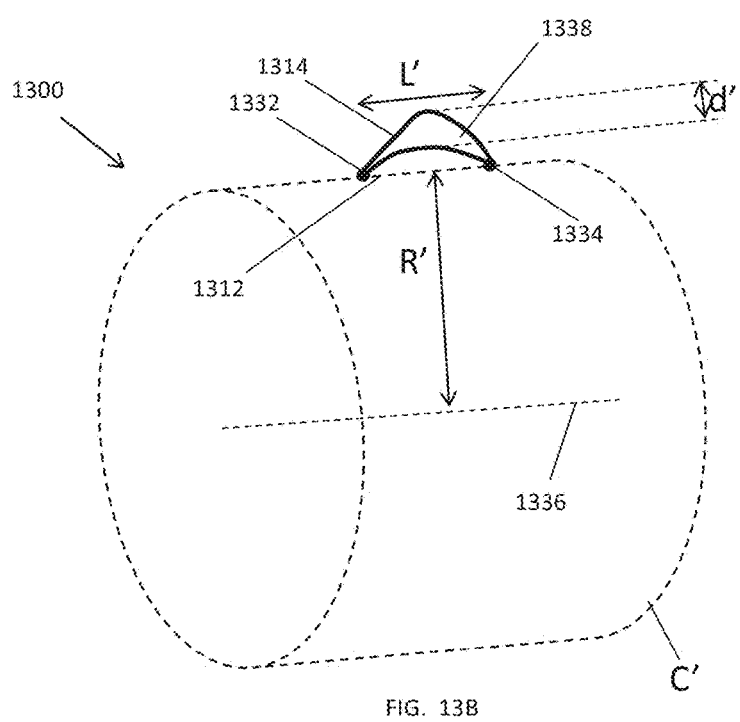
FIG. 13B is a simplified schematic side view of the device of FIG. 13A, after a space between wires has been enlarged, according to some embodiments of the invention.

FIG. 13B, is a simplified schematic side view of the device of FIG. 13A, after a space 1338 between wires has been enlarged, according to some embodiments of the invention.

In some embodiments, reducing a length (from L to L'; L<L') between connections 1332, 1334, increases a size of a space 1338 between wires 1312, 1314, in at least one dimension, where d is the radial dimension of space 1338 and d<d'. For example, as a length of first wire 1314 measured along a central axis of the first wire is longer than the length of second wire 1312 measured along a central axis of the second wire.

In some embodiments, a space 1338 is between two portions which protrude from cylinder C, for example, as illustrated in FIG. 13A where wire 1312 curves above a surface of cylinder C and in FIG. 13B where wire 1312 curves above a surface of cylinder C'.

In some embodiments, increasing radius R (e.g. from R to R') of device 1300, decreases the separation L (e.g. from L to L') between connections.

As mentioned previously, in some embodiments, expansion of a radius, R of the device (e.g. from R to R'; R<R' as illustrated in FIGS. 13A-B) where the radius is measured from a central longitudinal axis of the device 1336 decreases a length of device 1300. In some embodiments, cylinders C and C' are an outer surface or body of the device (e.g. excluding protrusions).

In some embodiments, device 1300 is cylindrical as illustrated in FIGS. 13A-B. In some embodiments, device, for example, has a non-cylindrical shape (e.g. as illustrated in FIG. 6A, as illustrated in FIG. 7B, as described herein) and cylinders C and C' are the largest diameter cylinders which are totally enclosed within the device.

Exemplary Wire Pairs Including Phase Differences

In some embodiments, an expandable structure includes one or more curved portion where the curved portions are spatially arranged on the structure such that there is a space between the curves. In an exemplary embodiment, a wire pair includes a first wire with a sinusoidal shaped portion and a second wire with a sinusoidal shaped portion, where the sinusoidal shaped portions are disposed on the expandable structure with a phase difference, the phase difference meaning that there is a space between the wires, in at least one dimension. In some embodiments, expanding the device (e.g. as described with reference to FIGS. 13A-B) increases the space between the wires.

Figure 14A:
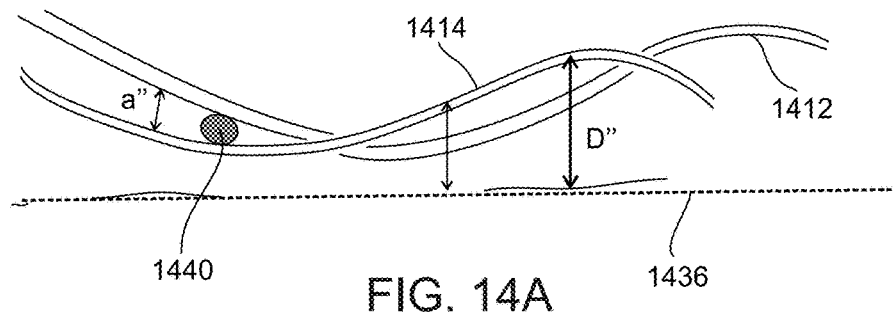
FIG. 14A is a simplified schematic side view of portion of a collapsed device including curved portions spatially arranged with a phase difference between the curved portions, according to some embodiments of the invention.

FIG. 14A is a simplified schematic side view of portion of a collapsed device including curved portions 1412, 1414 spatially arranged with a phase difference between the curved portions, according to some embodiments of the invention.

Figure 14B:
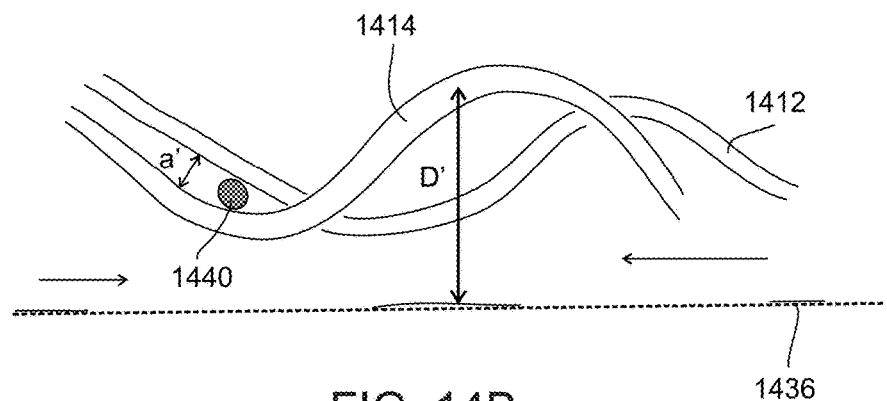
FIG. 14B is a simplified schematic side view of portion of an expanded device including curved portions spatially arranged with a phase difference between the curved portions, according to some embodiments of the invention.

FIG. 14B is a simplified schematic side view of portion of an expanded device including curved portions 1412, 1414 spatially arranged with a phase difference between the curved portions, according to some embodiments of the invention.

Figure 14C:
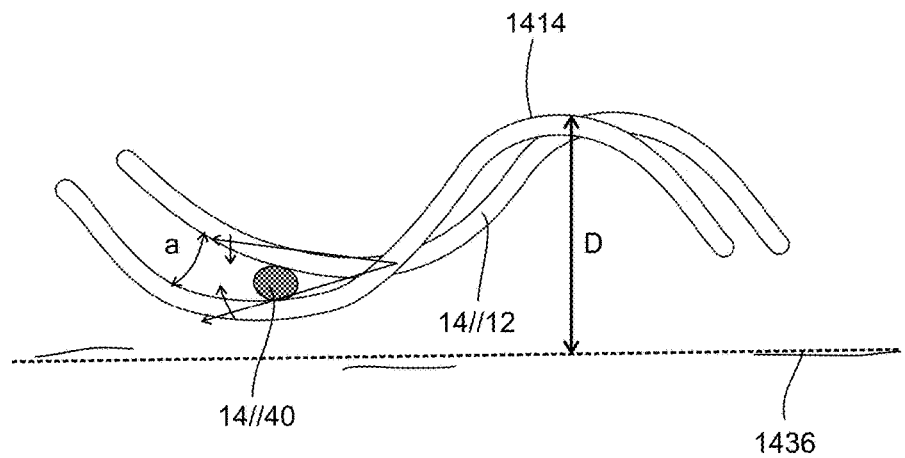
FIG. 14C is a simplified schematic side view of portion of a partially expanded and/or partially contracted device including curved portions spatially arranged with a phase difference between the curved portions, according to some embodiments of the invention.

FIG. 14C is a simplified schematic side view of portion of a partially expanded and/or partially contracted device including curved portions 1412, 1414 spatially arranged with a phase difference between the curved portions, according to some embodiments of the invention.

In some embodiments, dimension a" between the curved portions when the expandable structure is collapsed (radius of largest enclosed cylinder, is D" where line 1436 indicates a central longitudinal axis of the cylinder) is smaller than dimension a between the curved portions when the expandable structure is partially expanded (radius of largest enclosed cylinder is D) which is smaller than a dimension a' when the expandable structure is expanded (radius of largest enclosed cylinder is D"):

a"<a<a' and D"<D<D'.

In some embodiments, one or more spacer element 1440 (e.g. rod) is disposed between two or more portions of the device (e.g. wires) to maintain the phase difference between the wires. In some embodiments, rod/s are inserted into the structure, for example, during treatment (e.g. heat treatment). In some embodiments, rod/s are used in treatment to generate shape memory in wires including superelastic material (e.g. nitinol). In some embodiments, spacer element/s 1440 are removed during manufacture and/or before use of the device.

Figure 16:
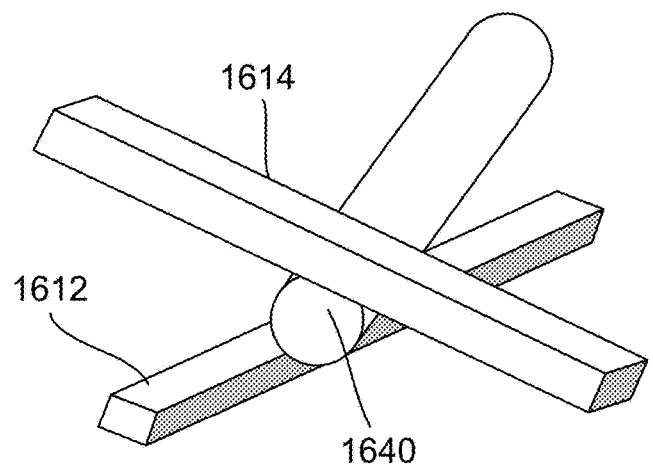
FIG. 16 is a simplified schematic side view of a portion of a device where a spacer rod holds a space between two portions of the device, according to some embodiments of the invention.

FIG. 16 is a simplified schematic side view of a portion of a device where a spacer rod 1640 holds a space between two portions 1612, 1614 of the device, according to some embodiments of the invention.

Exemplary Expandable Device Materials and Construction

In some embodiments, an expandable device (e.g. as described herein, e.g. as illustrated in FIGS. 6A-B and FIGS. 8A-B) is constructed using wires, for example a body of the device is constructed with a wire mesh (e.g. a woven mesh).

In some embodiments, at least a portion of the device includes flexible and/or elastic and/or biocompatible material e.g. nitinol, and/or cobalt chromium and/or stainless steel. In some embodiments, at least a portion of the device includes shape memory and/or superelastic material (e.g. nitinol).

In an exemplary embodiment, at least a portion of the device is constructed of nitinol wires.

In some embodiments, a portion of the device which captures obstructive material (e.g. an expandable structure) is constructed from wires of largest cross sectional dimension (e.g. diameter) 10-150 μm or 25-150 μm or 12-100 μm. In an exemplary embodiment, the device includes at least a portion constructed with 75 μm diameter wires. In an exemplary embodiment, the device includes at least a portion constructed with wires including a flattened cross sectional shape, e.g. a rounded shape with largest cross sectional dimension 100 μm and a cross sectional dimension perpendicular to the largest cross sectional dimension of 50 μm (e.g. "tape" including 50×100 μm cross section).

In some embodiments, additional material is added to a mesh device after it is constructed (e.g. by weaving). In some embodiments, one or more additional wire is woven onto an existing structure, for example, in some embodiments, one or more additional wire is wrapped around an existing wire.

Figure 15:
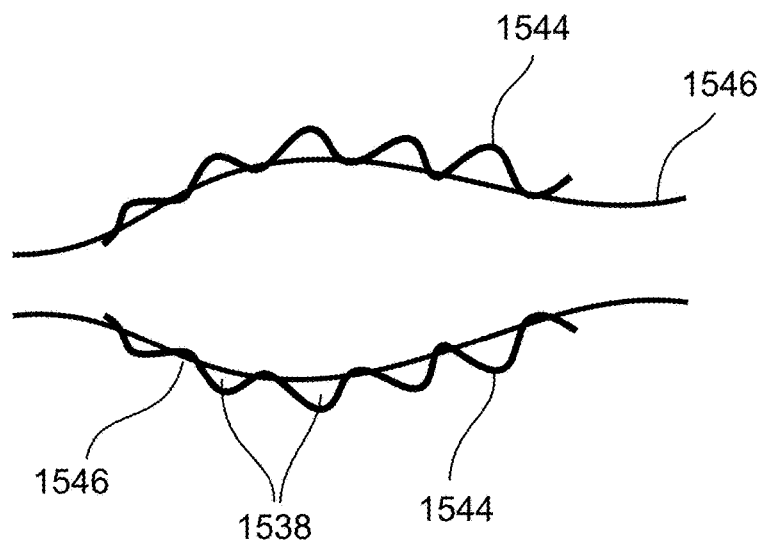
FIG. 15 is a simplified schematic side view of a portion of a device, including additional wires coupled to base wires, according to some embodiments of the invention.

FIG. 15 is a simplified schematic side view of a portion of a device, including additional wires 1544 coupled to base wires 1546, according to some embodiments of the invention. In some embodiments, spaces 1538 (e.g. as described herein) are formed between additional wire 1544 and base wire 1546.

Exemplary Treatments

In some embodiments, the device (e.g. as described herein) is used to remove blood clot material from a vessel. In an exemplary embodiment, the device (e.g. as described herein) is used to remove an obstruction (e.g. a clot) from a vessel in the brain, for example upon a stroke.

In some embodiments, additionally or alternatively, material other than blood clot material is removed e.g. fatty deposits and/or plaque and/or thrombus and/or platelet aggregate and/or foreign materials and/or calcified sediment. In this document the term "clot" or "clot material" is used to indicate any obstructive material within a vessel, fully and/or partially obstructing the vessel.

In some embodiments, the device (e.g. as described herein) is used to remove pulmonary embolism, and/or thrombus and/or occlusion. In some embodiments, the device (e.g. as described herein) is used to remove peripheral embolism, and/or thrombus and/or occlusion. In some embodiments, the device (e.g. as described herein) is used to remove cardiovascular embolism, and/or thrombus and/or occlusion. In some embodiments, the device (e.g. as described herein) is used in revascularization of hestenosis.

General

As used herein the term "about" and the term "approximately" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for removal of obstructive material from a vessel comprising:
    an expandable structure sized for insertion into the vessel; and
    one or more protrusion extending radially from a central longitudinal axis of said expandable structure such that a space is generated between said one or more protrusion and a closest portion of said expandable structure;
    wherein said space is sized and shaped to be suitable to accept obstructive material; and
    wherein said expandable structure includes a woven structure having warp and weft wires, said one or more protrusion is in the form of a wire with two ends, one end of said two ends forming said weft or warp wire of said woven structure and a second end of said two ends, opposite to said one end, forming a continuation of said weft or warp wire of said woven structure.

2. The device according to claim 1, wherein said device includes wires, wherein said one or more protrusion is a portion of a wire.

3. The device according to claim 1, wherein said space between said one or more protrusion and said closest portion of said expandable structure is enlarged by a separation between one or more portion of the device increasing at least in one dimension.

4. The device according to claim 3, wherein said separation comprises a radial component.

5. The device according to claim 3, wherein said separation comprises a component tangential to said central longitudinal axis of said device.

6. The device according to claim 3, wherein said separation comprises a component parallel to said central longitudinal axis of said device.

7. The device according to claim 1, wherein said space between said one or more protrusion and said closest portion of said expandable structure is reduced by a separation between one or more portion of the device decreasing at least in one dimension.

8. The device according to claim 1, wherein said one or more protrusion is rounded.

9. The device according to claim 1, wherein a radial component of said space is between 0.01-0.2 mm.

10. The device according to claim 1, wherein said central longitudinal axis of said expandable structure is a central longitudinal axis of a largest cylindrical space enclosable within said expandable structure.

11. The device according to claim 10, wherein said largest cylindrical space is a largest length cylindrical space enclosable within said expandable structure.

12. The device according to claim 10, wherein said largest cylindrical space is a largest diameter cylindrical space enclosable within said expandable structure.

13. The device according to claim 10, wherein said largest cylindrical space is a largest volume cylindrical space enclosable within said expandable structure.

14. The device according to claim 10,
    wherein said expandable structure is configured to have a collapsed state and a range of expanded shapes, wherein said expandable structure is expandable to a maximally expanded state,
    wherein a diameter of said largest cylindrical space in said collapsed state is smaller than a volume of said largest cylindrical space in said maximally expanded state.

15. The device according to claim 14, wherein said diameter of said largest cylindrical space in said collapsed space is 0.3-2 mm.

16. The device according to claim 15, wherein said diameter of said largest cylindrical space in said maximally expanded state is 1-7 mm.

17. The device according to claim 16, wherein a radial component of said space is larger when said expandable structure is in each of said range of expanded shapes than a radial component of said space when said device is in said collapsed state.

18. The device according to claim 1,
    wherein said one or more protrusion and said closest device portion are coupled at, at least two junctions, where an axial length of said one or more protrusion between said two junctions is longer than an axial length of said closest portion between said two junctions.

19. The device according to claim 1, wherein said
    one or more protrusion and said closest portion are curved spatially arranged to have a phase difference between said one or more protrusion and said closest portion.

20. The device according to claim 1, wherein said one or more protrusion includes a plurality of protrusions.

21. The device according to claim 20, wherein said plurality of protrusions are disposed at different radial positions around an axial location along said expandable structure.

22. The device according to claim 20, wherein one or more of said plurality of protrusions is dispersed at a different axial location along said expandable structure from one or more other of said plurality of protrusions.

23. The device according to claim 1,
wherein said expandable structure comprises:
said warp and weft wires are each coupled at a different radial position at a distal and a proximal end of said expandable structure,
wherein each said warp and weft wires transverses a path from said distal end to said proximal end including changes in radial position,
wherein, during said path, one or more of said warp and weft wires passes over one or more other of said warp and weft wires and under one or more other of said warp and weft wires,
wherein said warp and weft wires forms a tubular shaped mesh surface between said distal and proximal ends;
wherein at least one portion of one of said warp and weft wires includes said protrusion where said path departs protrudes radially away from said tubular shaped mesh surface and then extends axially, defining said space between said at least one portion of one of said warp and weft wiresand said tubular shaped mesh surface.

24. The device according to claim 23, wherein said path including changes in radial position is a helical path.

25. The device according to claim 1, comprising
said warp and weft wires are each coupled at a different radial position at a distal and a proximal end of said expandable structure; and
wherein each said warp and weft wires transverses a path from said distal end to said proximal end including changes in radial position;
wherein, during said path, one or more of said warp and weft wires passes over one or more other of said warp and weft wires and under one or more other wire;
wherein said warp and weft wires forms a tubular shaped mesh surface between said distal and proximal ends;
wherein at least one of said warp and weft wires includes said protruding portion.

26. The device according to claim 1 wherein said space is sized and shaped to be suitable to accept at least a portion of the obstructive material.

27. The device according to claim 1, wherein said one or more protrusion and said closest portion are attached to each other at two points located along said central longitudinal axis of said expandable structure, and wherein changing a distance between said two attachment points changes a size of said space.

28. The device according to claim 1, wherein said expandable structure is tubular and wherein said wire forming said one or more protrusion follows a path which departs from and returns to a surface of said expandable structure, extending radially away from said surface and axially along said central longitudinal axis of said expandable structure.

29. The device according to claim 1, wherein relative movement of said one or more protrusion and said closest portion pinches the obstructive material within said space.

30. The device of claim 1, wherein at least one of said warp and weft wires of said woven structure includes a curved section bridging sections of said wire and acting as said one or more protrusion.

31. The device of claim 1, wherein said one or more protrusion of said woven structure is formed by a curvature in said weft or warp wire.

* * * * *